(12) United States Patent
Pappou et al.

(10) Patent No.: US 12,427,022 B1
(45) Date of Patent: Sep. 30, 2025

(54) SYSTEMS AND METHODS OF THUMB CAROPMETACARPAL JOINTS IMPLANTS

(71) Applicant: SHOULDER HAND INNOVATIONS LLC, Odessa, FL (US)

(72) Inventors: Ioannis P. Pappou, Odessa, FL (US); Sergio Gutierrez, Tampa, FL (US)

(73) Assignee: SHOULDER HAND INNOVATIONS LLC, Odessa, FL (US)

( * ) Notice: Subject to any disclaimer, the term of this patent is extended or adjusted under 35 U.S.C. 154(b) by 0 days.

(21) Appl. No.: 18/948,149

(22) Filed: Nov. 14, 2024

(51) Int. Cl.
*A61F 2/42* (2006.01)
*A61F 2/30* (2006.01)

(52) U.S. Cl.
CPC .. *A61F 2/30724* (2013.01); *A61F 2002/4253* (2013.01)

(58) Field of Classification Search
CPC .. A61F 2/30724; A61F 2/4225; A61F 2/4241; A61F 2002/4228; A61F 2002/4233; A61F 2002/4238; A61F 2002/4243; A61F 2002/4251; A61F 2002/4253
See application file for complete search history.

(56) References Cited

U.S. PATENT DOCUMENTS

| | | | |
|---|---|---|---|
| 5,405,400 A | 4/1995 | Linscheid et al. | |
| 5,549,690 A * | 8/1996 | Hollister | A61L 27/446 623/901 |
| 8,167,952 B2 * | 5/2012 | Graham | A61F 2/4241 623/21.11 |
| 8,647,390 B2 * | 2/2014 | Bellemere | A61F 2/4241 623/21.16 |
| 8,715,362 B2 * | 5/2014 | Reiley | A61B 17/15 623/23.44 |
| 9,173,691 B2 | 11/2015 | Orbay et al. | |
| 2014/0194999 A1 | 7/2014 | Orbay et al. | |

* cited by examiner

*Primary Examiner* — Brian A Dukert
(74) *Attorney, Agent, or Firm* — FOLEY & LARDNER LLP

(57) ABSTRACT

An apparatus can include a metacarpal implant, a trapezium implant, and a spacer. The metacarpal implant can include a stem to be inserted into a first cavity of a metacarpal bone and having a first end and a second end, a radial lip, the radial lip extending from the second end, and an opening, the opening extending from the radial lip to the first end. The trapezium implant can include an implant head portion having a shape to match a shape of a trapezium bone and a first cavity insert, to be inserted into a second cavity of the trapezium bone extending from the bottom surface. The spacer can include a spacer head portion congruent to the implant head portion and an opening insert to be inserted in the opening and extending from the bottom surface.

19 Claims, 25 Drawing Sheets

SYSTEMS AND METHODS OF THUMB CAROPMETACARPAL JOINTS IMPLANTS

TECHNICAL FIELD

The present disclosure relates generally to implants for joint replacement.

BACKGROUND

Arthritis can occur with aging or repetitive movements and can cause severe pain and discomfort to individuals suffering from arthritis. Thumb arthritis can occur when cartilage wears away at the carpometacarpal (CMC) joint of the thumb. Options for those suffering from thumb arthritis can include ligament reconstruction, hematoma and distraction arthroplasty, and joint replacement surgery. Joint replacement surgery can also be performed in cases of joint deformities which can affect thumb function. However, joint replacement surgery can have complications such as impingement between a metacarpal and a trapezium bone of the thumb as well as friction between an implant and the bones.

SUMMARY

At least one aspect of the present disclosure is directed towards an apparatus, such as joint replacement apparatus or assembly. The apparatus can include a metacarpal implant. The metacarpal implant can include a stem to be inserted into a first cavity of a metacarpal bone and having a first end and a second end. The metacarpal implant can also include a radial lip, the radial lip extending from the second end and an opening, the opening extending from the radial lip to the first end. The apparatus can include a trapezium implant. The trapezium implant includes an implant head portion, the implant head portion having a top surface and a bottom surface, the top surface and the bottom surface being convex on a first plane and concave on a second plane, the top surface having a smooth shape and the bottom surface having a shape to match a shape of a trapezium bone and a first cavity insert, to be inserted into a second cavity of the trapezium bone extending from the bottom surface. The apparatus can also include a spacer. The spacer can include a spacer head portion congruent to the implant head portion, the spacer head portion having a top surface and a bottom surface, the top surface having a smooth shape and being convex on a third plane and concave on a fourth plane and an opening insert to be inserted in the opening and extending from the bottom surface.

In some implementations, the metacarpal implant and the trapezium implant can include at least one of titanium, ceramic, or pyrolytic carbon. The spacer can include at least one of plastic, metal, or ceramic. The bottom surface of the implant head portion can include cobalt chrome (CoCr) on highly crosslinked polyethylene (HCPE). The trapezium implant can include a second cavity insert, the second cavity insert extending from the bottom surface, the first cavity insert extending along a first axis and the second cavity insert extending along a second axis, the first axis and the second axis offset from each other and parallel. The metacarpal implant can further include a first aperture and a second aperture located on opposite sides of the radial lip.

In some implementations, the top surface of the spacer head portion and the top surface of the implant head portion are congruent. The implant head portion can further include a first aperture and a second aperture, the first and the second aperture disposed on a first lateral surface and a second lateral surface of the implant head portion, the first lateral surface and the second lateral surface being opposite each other. The stem and the first cavity can be congruent. The opening insert and the stem can be threadedly coupled by a first threaded portion of the opening insert and a portion of an inner surface of the stem having a second threaded portion.

In some implementations, a first end of the spacer head portion extends further away from the opening insert than a second end of the spacer head portion. A first portion of the radial lip can extend further away from the stem than a second portion on the radial lip. The opening can include a first portion, a second portion, and a third portion, the first portion located within the radial lip and the second portion and the third portion located within the stem.

At least one aspect of the present disclosure is directed towards a method. The method can include resecting a portion of a metacarpal bone to create a first cavity. The method can also include resecting a portion of a trapezium bone to create a second cavity. The method can further include inserting, a metacarpal implant and a spacer, the spacer coupled to the metacarpal implant, the metacarpal implant being inserted until a stem of the metacarpal implant contacts an inner surface of the first cavity. The method can include inserting, a trapezium implant, the trapezium implant being inserted until a first cavity insert of the trapezium implant contacts an inner surface of the second cavity and aligning, a top surface of the spacer and a top surface of the trapezium implant.

In some implementations, the method further includes resecting the portion of the trapezium bone to create a third cavity and inserting, the trapezium implant, the trapezium implant being inserted until the first cavity insert and a second cavity insert of the trapezium implant contacts the inner surface of the second cavity and an inner surface of the third cavity. The method can include contouring a first surface of the trapezium bone to form a mating engagement the trapezium implant with the trapezium bone. The method can also include contouring the inner surface of the first cavity to form a mating engagement the metacarpal implant with the metacarpal bone. The method can include resecting the portion of the metacarpal bone to create the first cavity further comprises starting resection at a second surface of the metacarpal bone facing the trapezium bone. The method can also include resecting the portion of the trapezium bone to create the second cavity further comprises starting resection at a third surface of the trapezium bone facing the metacarpal bone.

At least one aspect of the present disclosure is directed towards a kit. The kit can include a rasp, a contouring tool, and a prosthesis. The prosthesis can include a metacarpal implant to be inserted into a first cavity of a metacarpal bone, a trapezium implant comprising a surface to match a shape of a trapezium bone and an insert to be inserted into a second cavity of the trapezium bone, and a spacer to couple with the metacarpal implant and the trapezium implant.

BRIEF DESCRIPTION OF THE DRAWINGS

The foregoing and other features of the present disclosure will become more fully apparent from the following description and appended claims taken in conjunction with the accompanying drawings. Understanding that these drawings depict only several implementations in accordance with the disclosure and are therefore not to be considered limiting of its scope, the disclosure will be described with additional specificity and detail through use of the accompanying drawings.

Figure 1:
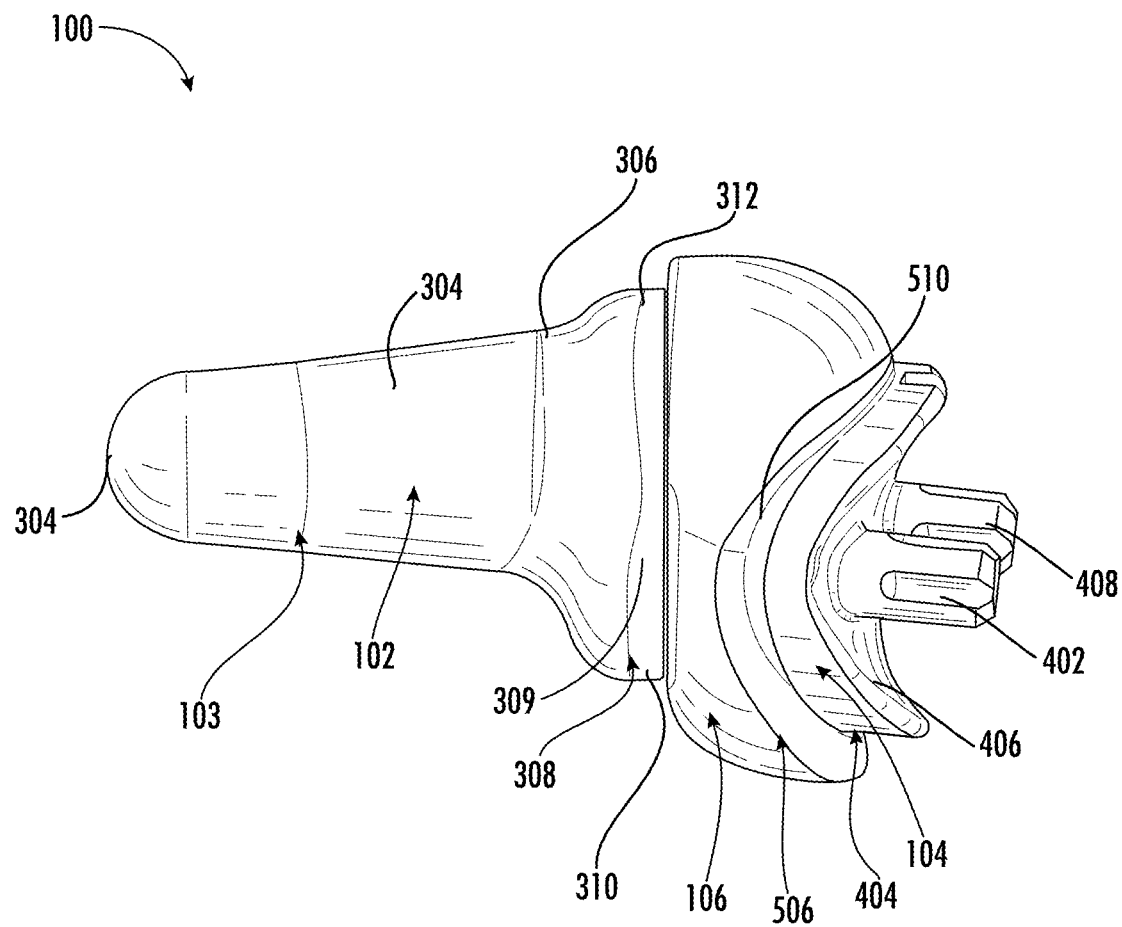
FIG. 1 is a side view of an implant system.

Reference is made to the accompanying drawings throughout the following detailed description. In the drawings, similar symbols typically identify similar components unless context dictates otherwise. The illustrative implementations described in the detailed description, drawings, and claims are not meant to be limiting. Other implementations can be utilized, and other changes can be made, without departing from the spirit or scope of the subject matter presented here. It will be readily understood that the aspects of the present disclosure, as generally described herein and illustrated in the figures, can be arranged, substituted, combined, and designed in a wide variety of different configurations, all of which are explicitly contemplated and made part of this disclosure.

DETAILED DESCRIPTION

Following below are more detailed descriptions of various concepts related to, and implementations of a joint replacement apparatus. The various concepts introduced above and discussed in greater detail below can be implemented in any of a number of ways, as the described concepts are not limited to any particular manner of implementation. Examples of specific implementations and applications are provided primarily for illustrative purposes.

I. Overview

CMC replacement implants may fail to recreate an anatomy of the CMC joint. Not preserving the anatomy of the CMC joint can result in loosening or dislocation of the implants within the thumb. Conventional methods can include performing a trapeziectomy (e.g., removing a trapezium bone in the thumb), and then suspending a metacarpal bone of the thumb to prevent subsidence (e.g., sinking, settling of joint implant which can comprise function of the implant). Methods of suspending the metacarpal bone can include bone fixation, tendon grafts, ligament reconstruction, etc. However, the conventional methods may not fully replicate function of the trapezium bone and is not ideal to accept axial loads (e.g., along a length of the thumb, in a direction from the metacarpal bone to distal phalanges). For example, suspension methods can fail by friction between the metacarpal bone or by subsidence of the metacarpal making the conventional methods nonideal for axial loads. In addition, conventional methods can involve materials with higher coefficients of friction (e.g., metal) which can result in suspension failure.

Implementations herein are directed towards implementations of implants for CMC joints that can preserve the anatomy of the CMC joint, can provide durable long-term fixation, and can have congruent, low-friction outer surfaces. For example, an outer surface of the implants can include cobalt chrome (CoCr) on highly crosslinked polyethylene (HCPE), which has a low coefficient of friction compared to, for example, metal. The lower coefficient of friction can provide increased pain relief compared to implants composed of metal. Additionally, by preserving the anatomy of the CMC joint, friction is reduced and thus enables the implants ideal to accept axial loads.

For example, an apparatus can include a metacarpal implant, a trapezium implant, and a spacer. The trapezium implant can include metal and have a saddle-shaped concavity that achieves ingrowth of the trapezium bone on the concavity while having a smooth, articular surface towards the CMC joint. Bone ingrowth can secure the trapezium implant to the trapezium bone. The articular surface can include CoCr on HCPE to reduce a friction between the trapezium implant and the trapezium bone. The trapezium implant can be congruent to a joint surface of the trapezium bone. Fixation of the trapezium implant to the trapezium bone can be though a keel or pegs. The metacarpal implant can be modular, and include a stem inserted into a shaft of the metacarpal bone. Insertion of the stem can allow for bone ingrowth of the metacarpal bone to the metacarpal implant. The shaft can be resected from the metacarpal bone. The stem can be inserted into the shaft and achieve fixation by being press fit to an endosteal surface of the stem. An outer surface of the metacarpal implant can include CoCr on HCPE. In some implementations, the stem and the shaft include threads. The spacer can be disposed between the metacarpal implant and the trapezium implant. The spacer can include polyethylene (PE) and can be coupled to the stem via press fit or a snap fit ring. The apparatus can preserve the anatomy of the CMC joint. By preserving the anatomy of the CMC joint, the apparatus can also enable long-term, durable bone fixation via bone ingrowth. Furthermore, preservation of the anatomy can also enable the bones to absorb loads and prevent subsidence of the metacarpal bone and maintain a center of rotation of the CMC joint.

III. Overview of a CMC Joint Implant Apparatus

Figure 2:
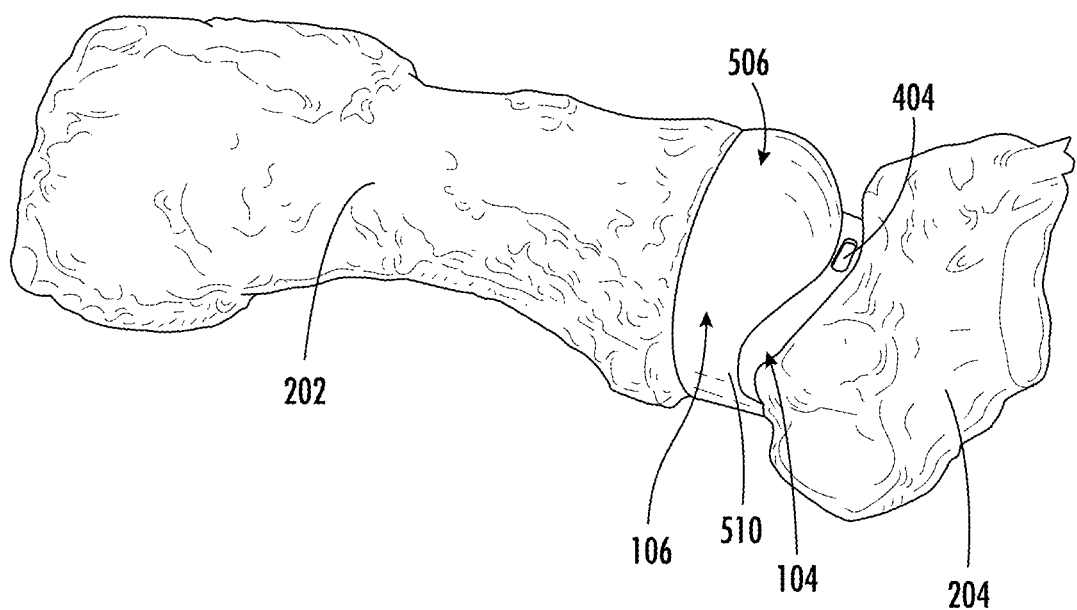
FIG. 2 is a perspective view of the implant system of FIG. 1 coupled to a metacarpal bone and a trapezium bone.
Figure 3:
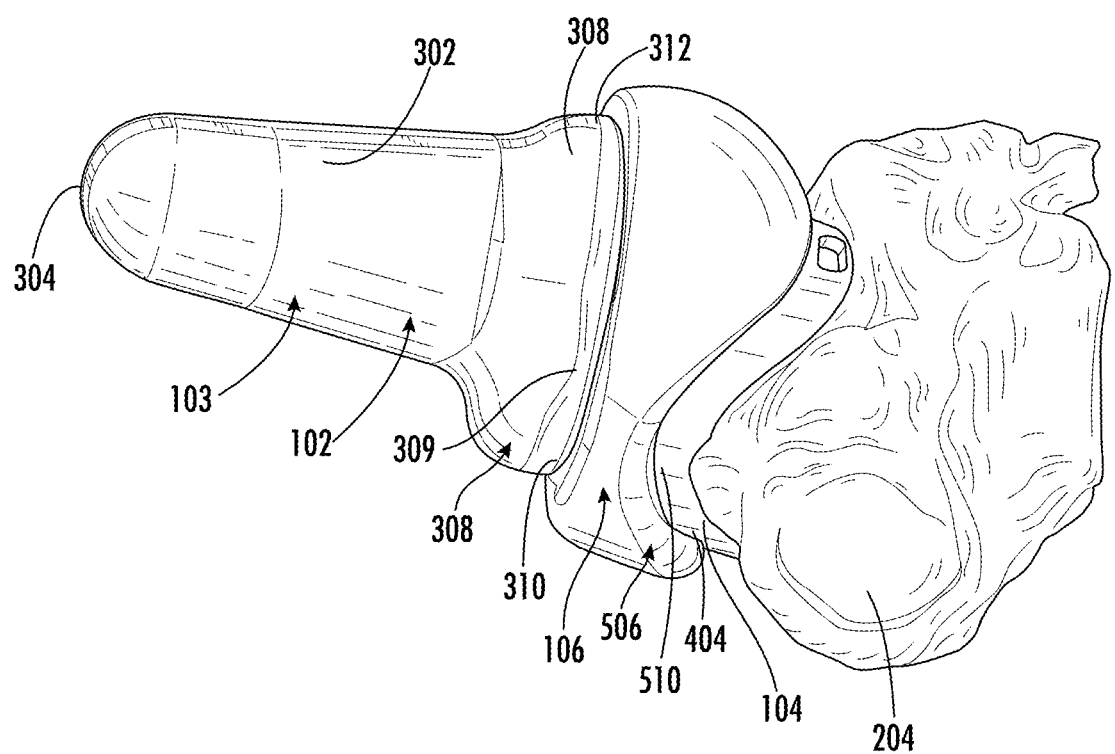
FIG. 3 is a perspective view of the implant system of FIG. 1 coupled to the trapezium bone.
Figure 4:
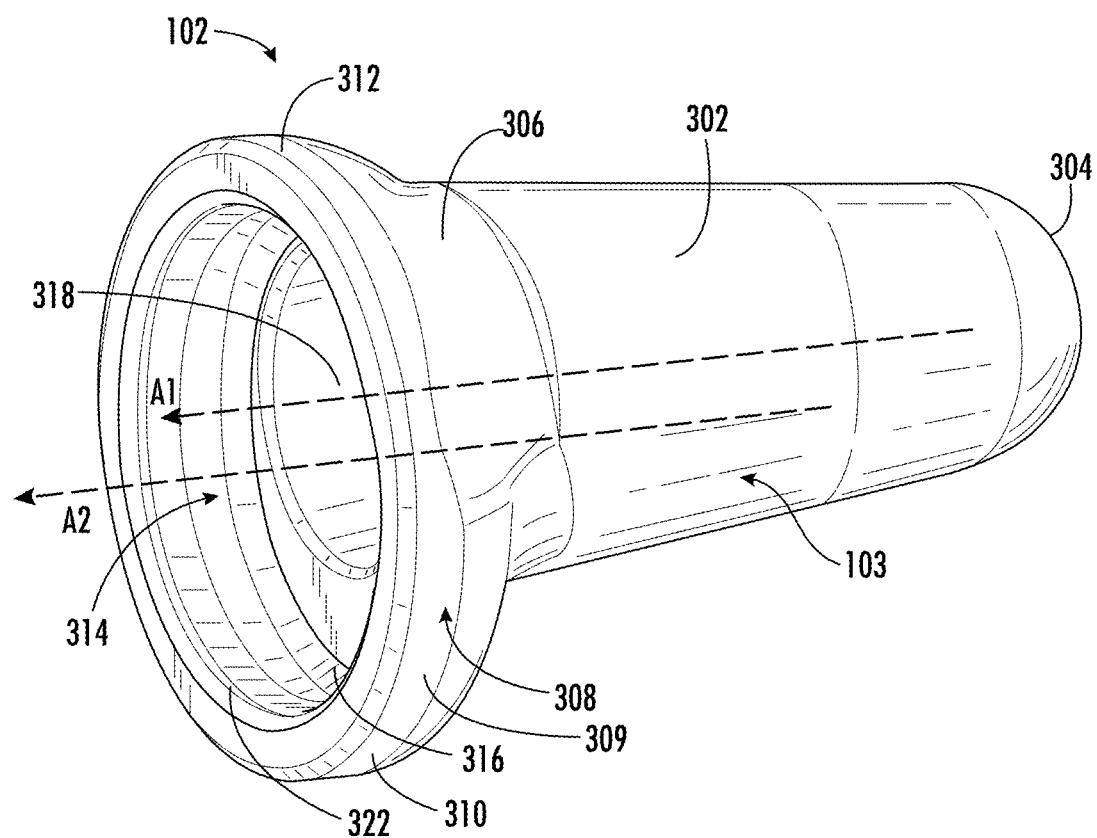
FIG. 4 is a perspective view of a metacarpal implant.
Figure 5:
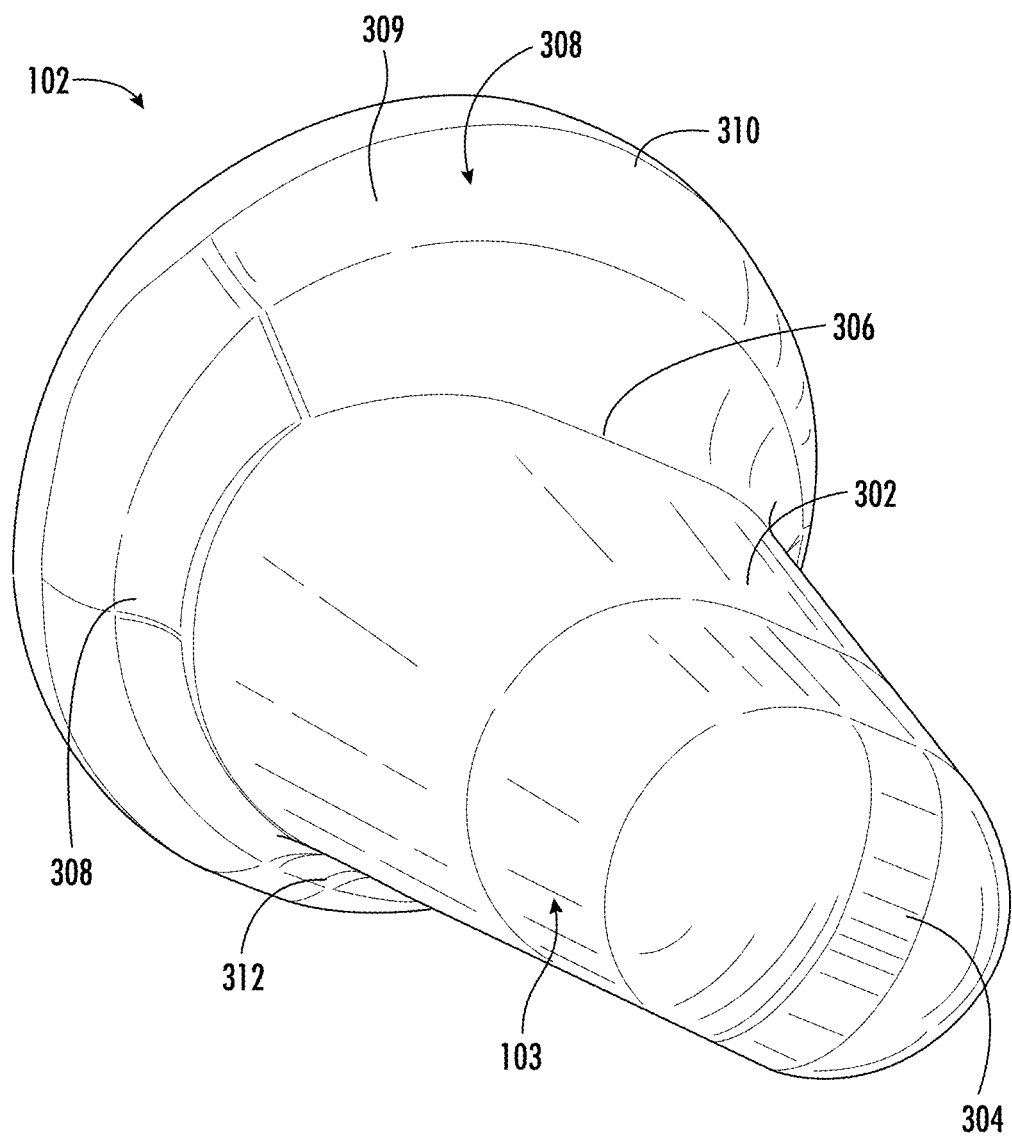
FIG. 5 is another perspective view of the metacarpal implant of FIG. 4.
Figure 6:
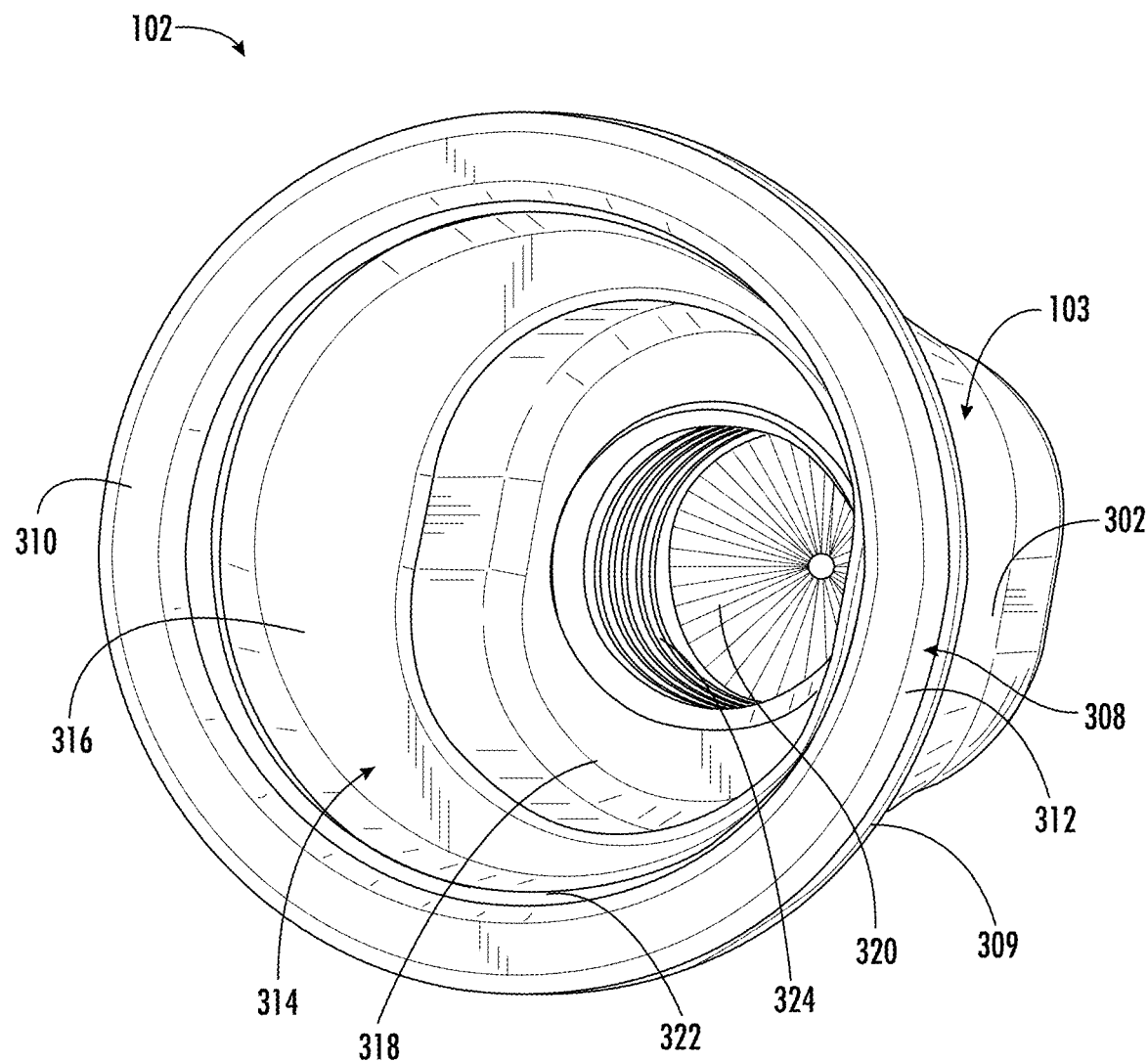
FIG. 6 is another perspective view of the metacarpal implant of FIG. 4.
Figure 7:
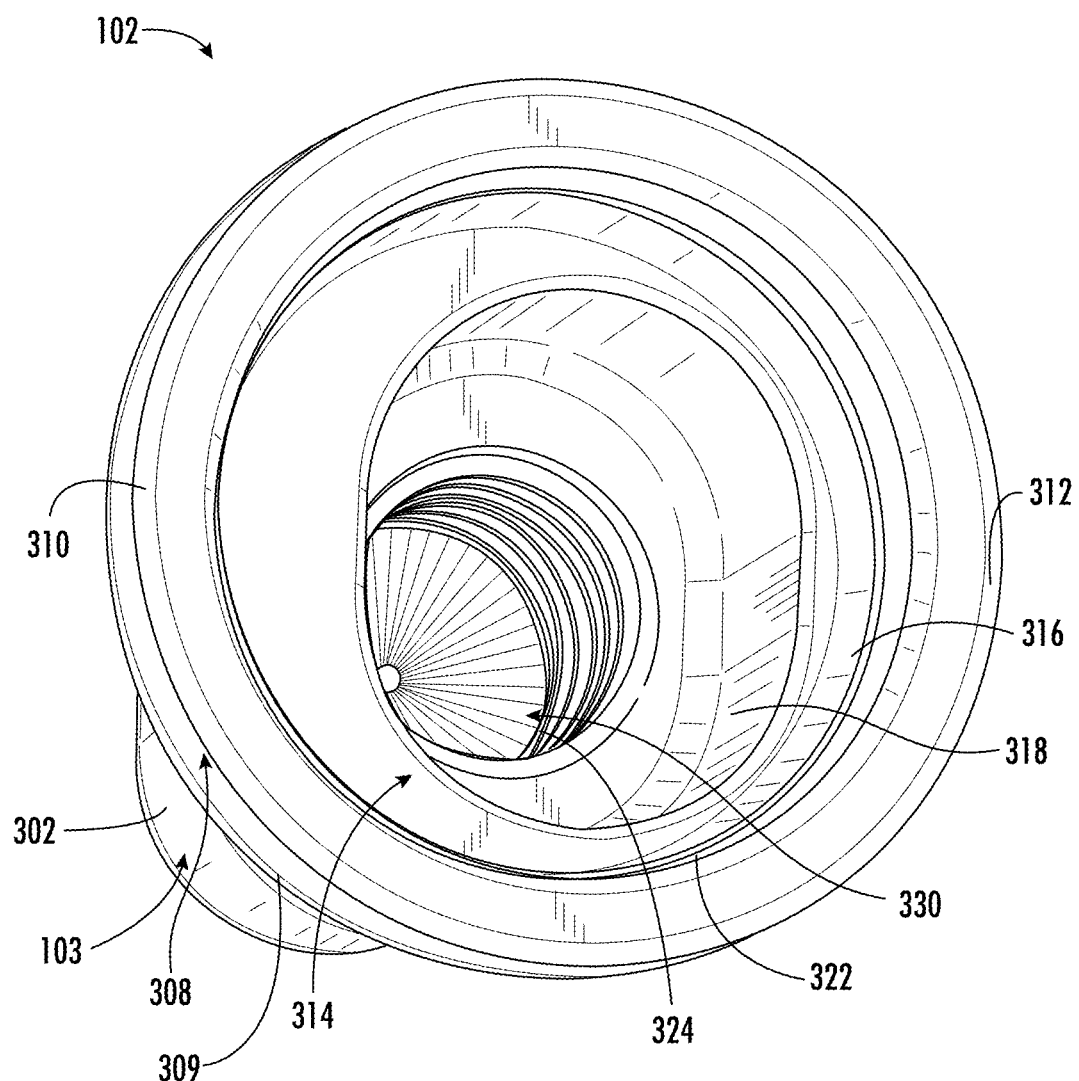
FIG. 7 is another perspective view of the metacarpal implant of FIG. 4.

FIGS. 1-3 show various views of an example of an implant apparatus 100 (e.g., a CMC joint implant apparatus, a prosthesis). The CMC joint implant apparatus 100 will herein be referred to as the implant apparatus 100. The implant apparatus 100 can be used to replace a CMC joint during joint replacement surgery. The implant apparatus 100 can be inserted into and coupled to a metacarpal bone 202 and a trapezium bone 204 of a thumb. The implant apparatus 100 can replicate an anatomy of the CMC joint. By replicating the anatomy of the CMC joint, the implant apparatus 100 reduces friction and supports axial loads to the thumb.

Figure 8:
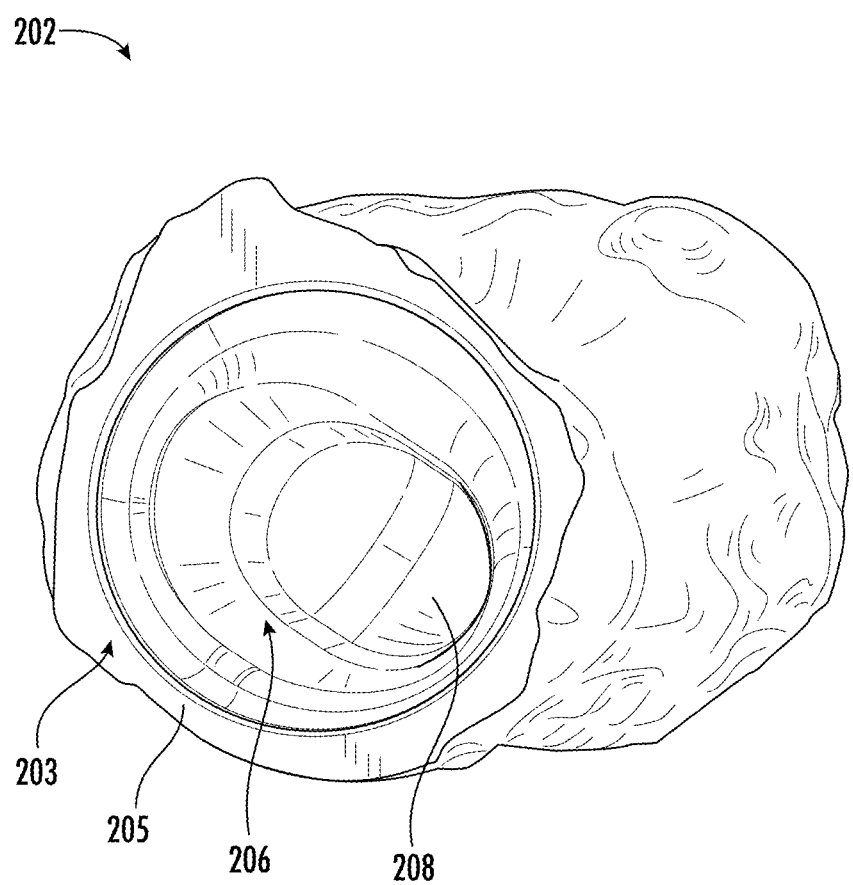
FIG. 8 is a perspective view of a cavity of the metacarpal bone.
Figure 9:
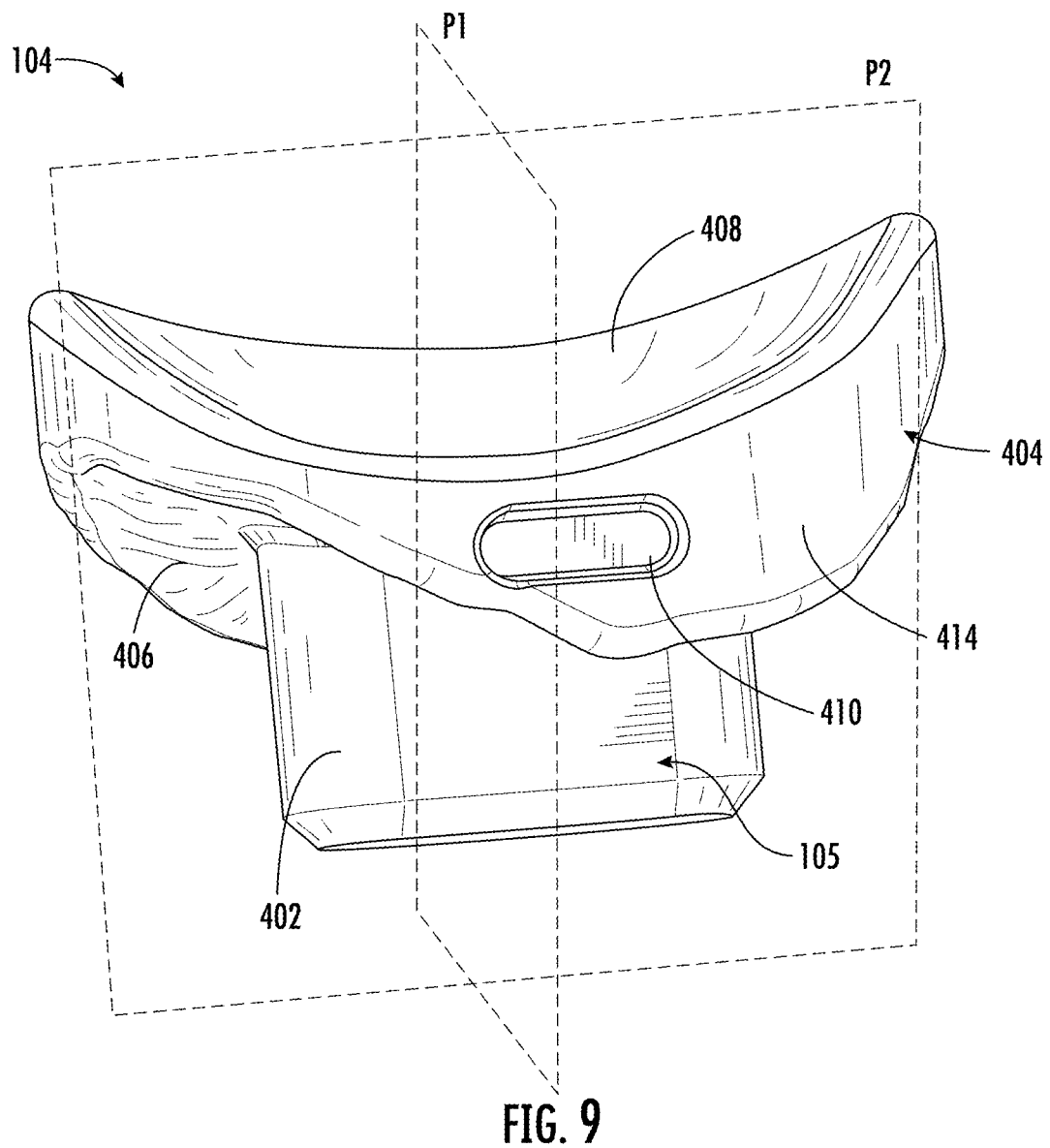
FIG. 9 is a perspective view of a trapezium implant.

The implant apparatus 100 can include a metacarpal implant 102. The metacarpal implant 102 is shown in greater detail in FIGS. 4-7. The metacarpal implant 102 can replicate the anatomy of the CMC joint. The metacarpal implant 102 can be inserted into the metacarpal bone 202. The metacarpal bone 202 can include a first cavity 206, shown in FIG. 8, in which the metacarpal implant 102 is inserted into. The first cavity 206 can be created by resecting a portion 203 of the metacarpal bone 202. Resecting can be performed with a rasp. The rasp can be included in a kit. Resection of the first cavity 206 can begin at a surface 205 of the metacarpal bone 202 facing the trapezium bone 204. The first cavity 206 can be centered on a first axis A1.

The metacarpal implant 102 can include or be made from materials including, but not limited to, titanium, ceramic, pyrolytic carbon, metal, or composites, or various combinations thereof, among others. An outer surface 103 of the metacarpal implant 102 can include cobalt chrome (CoCr) on highly crosslinked polyethylene (HCPE). CoCr on HCPE has a lower coefficient of friction than titanium. The outer surface 103 can reduce a friction between the metacarpal implant 102 and the metacarpal bone 202 (e.g., compared to titanium). The outer surface 103 can be in contact with the metacarpal bone 202. The outer surface 103 can be smooth. The metacarpal implant 102 can include an integrated partial bone-side porous surface or an integrated full bone-side porous surface to facilitate bone ingrowth. For example, the outer surface 103 can be at least partially porous. In some implementations, a porous surface (e.g., the outer surface 103) of the metacarpal implant 102 may be applied with a secondary process such as a surface coating (e.g., calcium phosphate coating), a biochemical surface treatment (e.g., growth factor coating), sandblasted, or a biodegradable coating (e.g., polymer coating with bioactive agents).

The metacarpal implant 102 can include a stem 302. The stem 302 can be inserted into the first cavity 206. The stem 302 can have an elliptic cylindrical shape. In some implementations, the stem 302 has a cylindrical shape. The stem 302 can be congruent to the first cavity 206 (e.g., have a same shape). In some implementations, the stem 302 is press fit to the first cavity 206. As shown in, for example, FIG. 4, the stem 302 can be centered on the first axis A1. The stem 302 can include a first end 304. The metacarpal implant 102 can be inserted into the first cavity 206 until the first end 304 contacts a bottom surface (e.g., endosteal surface, inner surface) 208 of the first cavity 206. In some implementations, the first cavity 206 is contoured by a contouring tool to form a mating engagement with the stem 302 and the first cavity 206. The contouring tool can be included in the kit. The stem 302 being press fit and congruent to the first cavity 206 can enable long-term fixation of the metacarpal implant 102 via bone ingrowth of the metacarpal bone 202.

The stem 302 can include a second end 306, opposite the first end 304. The metacarpal implant 102 can include a radial lip 308. The radial lip 308 can extend from the second end 306. The radial lip 308 can extend around a perimeter of the second end 306. The radial lip 308 can have a circular shape. In some implementations, the radial lip 308 can have an elliptic shape. The radial lip 308 is centered on a second axis A2. The radial lip 308 can extend radially outwards and away from the second axis A2. The second axis A2 is parallel to and offset from the first axis A1. In some implementations, the second axis A2 is co-axial and skewed relative to the first axis A1. In some implementations, an outer surface 309 of the radial lip 308 has a shape matching the surface 205. The outer surface 309 can be congruent to the surface 205. The outer surface 309 can be a polished surface. The outer surface 309 can have a secondary process applied to decrease friction, such as but not limited to, surface coatings (e.g., titanium nitride), polishing (e.g., electropolishing), or surface texturing (e.g., grooving texturing), among others.

The radial lip 308 can include a first portion 310. The radial lip 308 can also include a second portion 312. As shown in, for example, FIG. 4, the first portion 310 can extend further away from the stem 302 (e.g., the first axis A1) than the second portion 312. The first portion 310 and the second portion 312 can be equidistant from the second axis A2. In some implementations, the first portion 310 and the second portion 312 are equidistant from the stem 302. In some implementations, the metacarpal implant 102 does not include the radial lip 308.

The metacarpal implant 102 can also include an opening 314. The opening 314 can extend from the radial lip 308 to the first end 304. As shown in, for example, FIGS. 6-7, the opening 314 can include one or more portions. The opening 314 can include a first portion 316, a second portion 318, and a third portion 320. The first portion 316 can be located within the radial lip 308. The first portion 316 can be congruent with an inner surface 322 of the radial lip 308. The first portion 316 can have a circular shape. The first portion 316 can be centered on the second axis A2. The second portion 318 can extend from the first portion 316 along the first axis A1 towards the first end 304. The second portion 318 can have an elliptic cylindrical shape. In some implementations, the second portion 318 has a circular shape. The second portion 318 can be located within the stem 302. A size (e.g., diameter, length, width) of the second portion 318 can be less than the first portion 316. The third portion 320 can extend from the second portion 318 along the first axis A1 towards the first end 304. The third portion 320 can have a circular shape. In some implementations, the third portion 320 has an elliptic cylindrical shape. The third portion 320 can be located within the stem 302. A size of the third portion 320 can be less than the size of the first portion 316 and the second portion 318. The third portion 320 can include a first threaded portion 324. The first threaded portion 324 can facilitate insertion and extraction of the stem 302.

Figure 14:
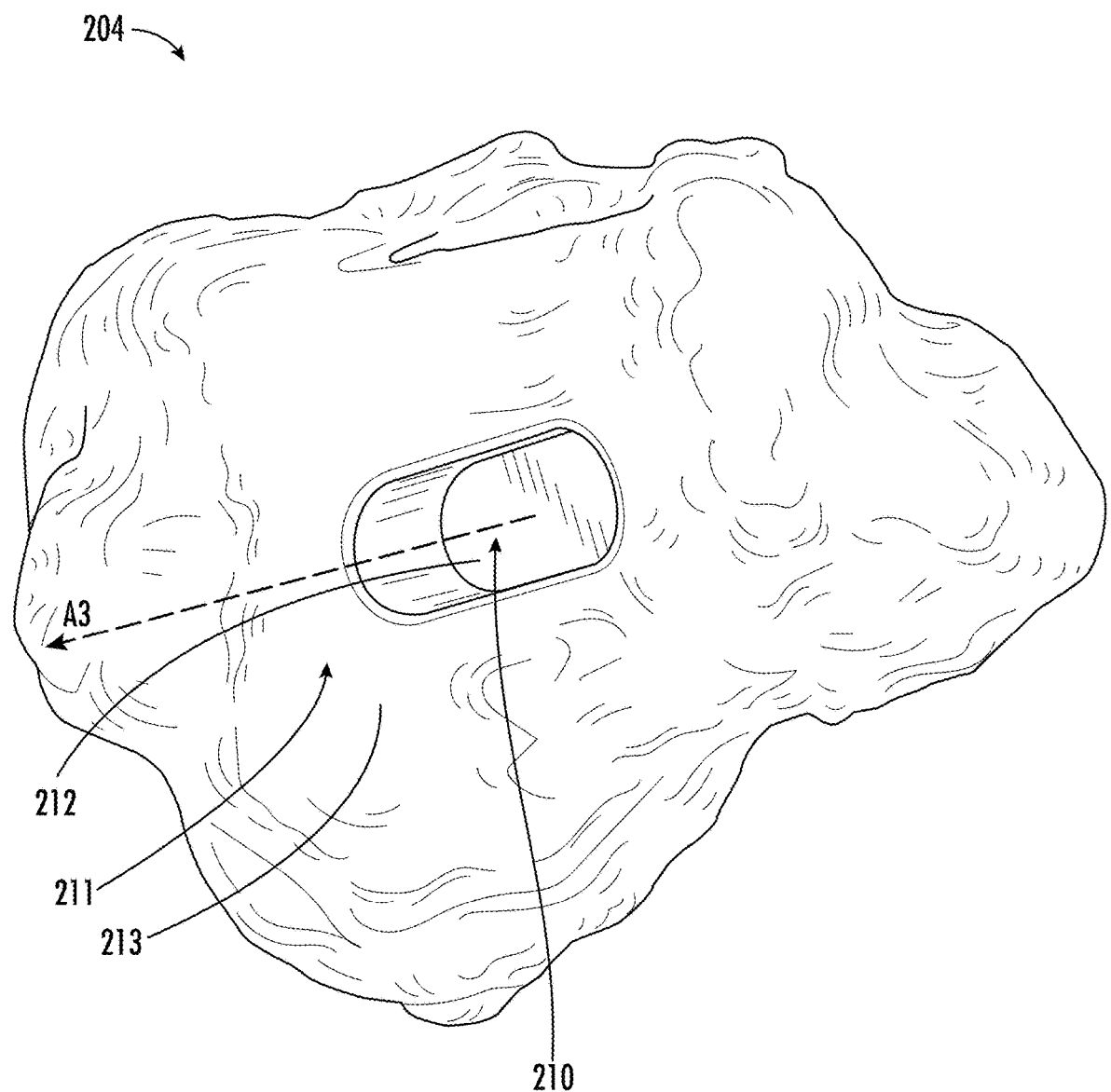
FIG. 14 is a perspective view of a cavity of the trapezium bone.

The implant apparatus 100 can include a trapezium implant 104. One implementation of the trapezium implant 104 is shown in greater detail FIGS. 9-13. The trapezium implant 104 can be inserted into the trapezium bone 204. The trapezium bone 204 can include a second cavity 210, shown in FIG. 14, in which the trapezium implant 104 is inserted into. The second cavity 210 can be created by resecting a portion 211 of the trapezium bone 204. Resecting can be performed with the rasp. Resection can begin at a surface 213 of the trapezium bone 204 facing the metacarpal bone 202. The second cavity 210 can have an elliptic cylindrical shape. The second cavity 210 can be centered on a third axis A3. The third axis A3 can be parallel to and offset from the first axis A1 and the second axis A2. In some implementations, the third axis A3 is co-axial and skewed relative to the first axis A1 and the second axis A2. The trapezium implant 104 can include, but not limited to, titanium, ceramic, pyrolytic carbon, metal, or composites. An outer surface 105 of the trapezium implant 104 can include CoCr on HCPE. The outer surface 105 enables a reduced friction between the trapezium implant 104 and the trapezium bone 204 (e.g., compared to titanium). The trapezium implant 104 can include either an integrated partial bone-side porous surface or an integrated full bone-side porous surface to promote bone ingrowth. For example, the outer surface 105 is porous. In some implementations, a porous surface (e.g., the outer surface 105) of the trapezium implant 104 may be applied with a secondary process such as a surface coating (e.g., calcium phosphate coating), a biochemical surface treatment (e.g., growth factor coating), sandblasted, or a biodegradable coating (e.g., polymer coating with bioactive agents).

The trapezium implant 104 can include a first cavity insert 402 (e.g., keel, protrusion). The first cavity insert 402 can be inserted into and in contact with a bottom surface 212 (e.g., endosteal surface, inner surface) of the second cavity 210. The trapezium implant 104 can be inserted into the second cavity 210 until the first cavity insert 402 contacts the bottom surface 212. The first cavity insert 402 can be configured to fixate (e.g., couple) the trapezium implant 104 to the trapezium bone 204. The first cavity insert 402 can be congruent to the second cavity 210. The first cavity insert 402 can have an elliptic cylindrical shape. In some implementations, the first cavity insert 402 is press fit into the second cavity 210. The first cavity insert 402 can be centered on the third axis A3. The first cavity insert 402 can enable long-term fixation via bone ingrowth by being inserted into and congruent to the second cavity 210.

The trapezium implant 104 can include an implant head portion 404. The first cavity insert 402 can extend from the implant head portion 404. The implant head portion 404 can have a bottom surface 406. The first cavity insert 402 can extend from the bottom surface 406. The bottom surface 406 can face the trapezium bone 204. The bottom surface 406 can be in contact with the trapezium bone 204. As shown in, for example, FIGS. 11-12, the bottom surface 406 can have a shape that matches a shape of the trapezium bone 204. For example, the bottom surface 406 has a shape that matches the surface 213 (e.g., articular surface) of the trapezium bone 204. In some implementations, the surface 213 is contoured to form a mating engagement with (e.g., be congruent to) the bottom surface 406. The surface 213 can be contoured with a contouring tool. The bottom surface 406 can include CoCr on HCPE. The implant head portion 404 can have a top surface 408. The top surface 408 can face opposite the bottom surface 406. The top surface 408 can have a smooth shape. The top surface 408 can include titanium. In some implementations, the top surface 408 can include CoCr on HCPE. The top surface 408 can be a polished surface. The top surface 408 can have a secondary process applied to decrease friction, such as but not limited to, surface coatings (e.g., titanium nitride), polishing (e.g., electropolishing), or surface texturing (e.g., grooving texturing), among others.

The implant head portion 404 can replicate the anatomy of the CMC joint. The implant head portion 404 can be saddle shaped. As shown in, for example, FIG. 10, the top surface 408 and the bottom surface 406 can be convex on a first plane P1. The top surface and the bottom surface 406 can be concave on a second plane P2. In some implementations, the top surface 408 is convex on the first plane P1 and concave on the second plane P2. In some implementations, the bottom surface 406 is convex on the first plane P1 and concave on the second plane P2.

Figure 10:
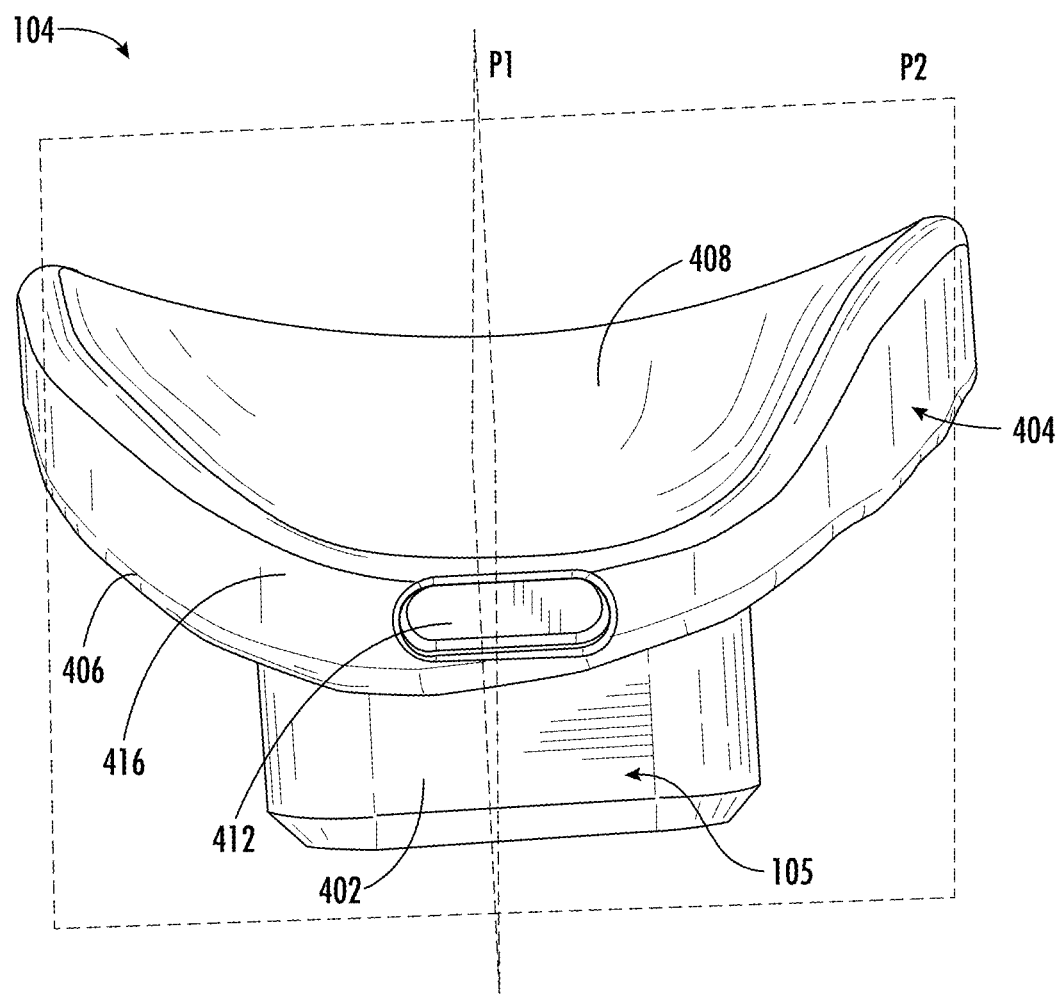
FIG. 10 is a front view of the trapezium implant of FIG. 9.
Figure 11:
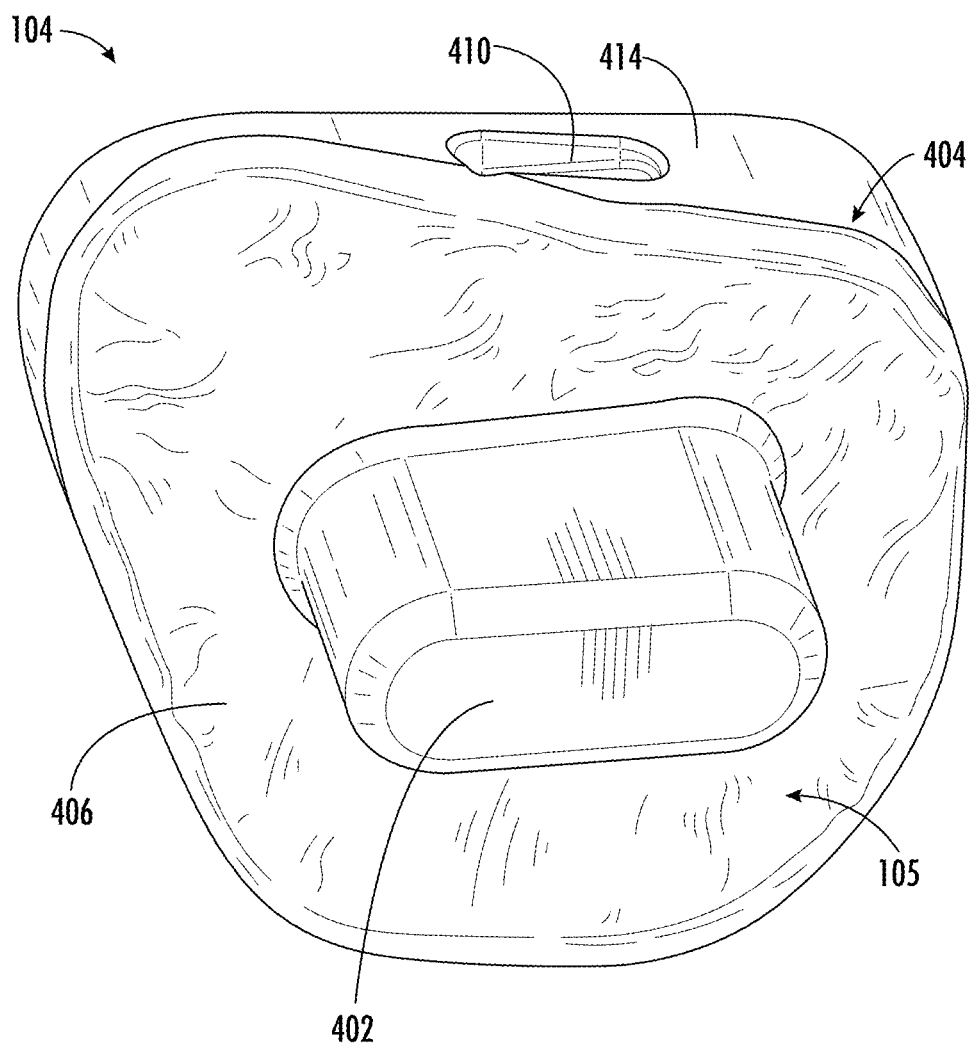
FIG. 11 is another perspective view of the trapezium implant of FIG. 9.
Figure 12:
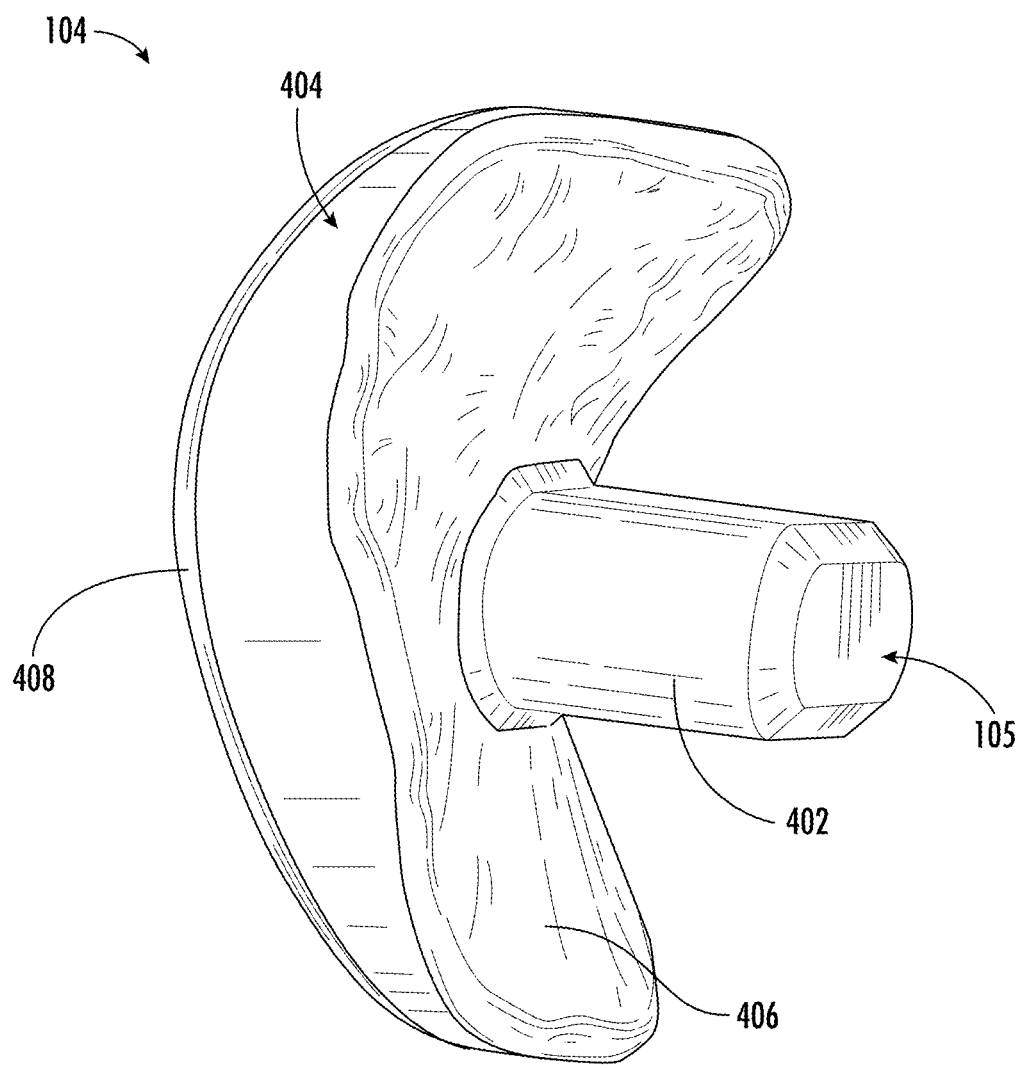
FIG. 12 is a side view of the trapezium implant of FIG. 9.
Figure 13:
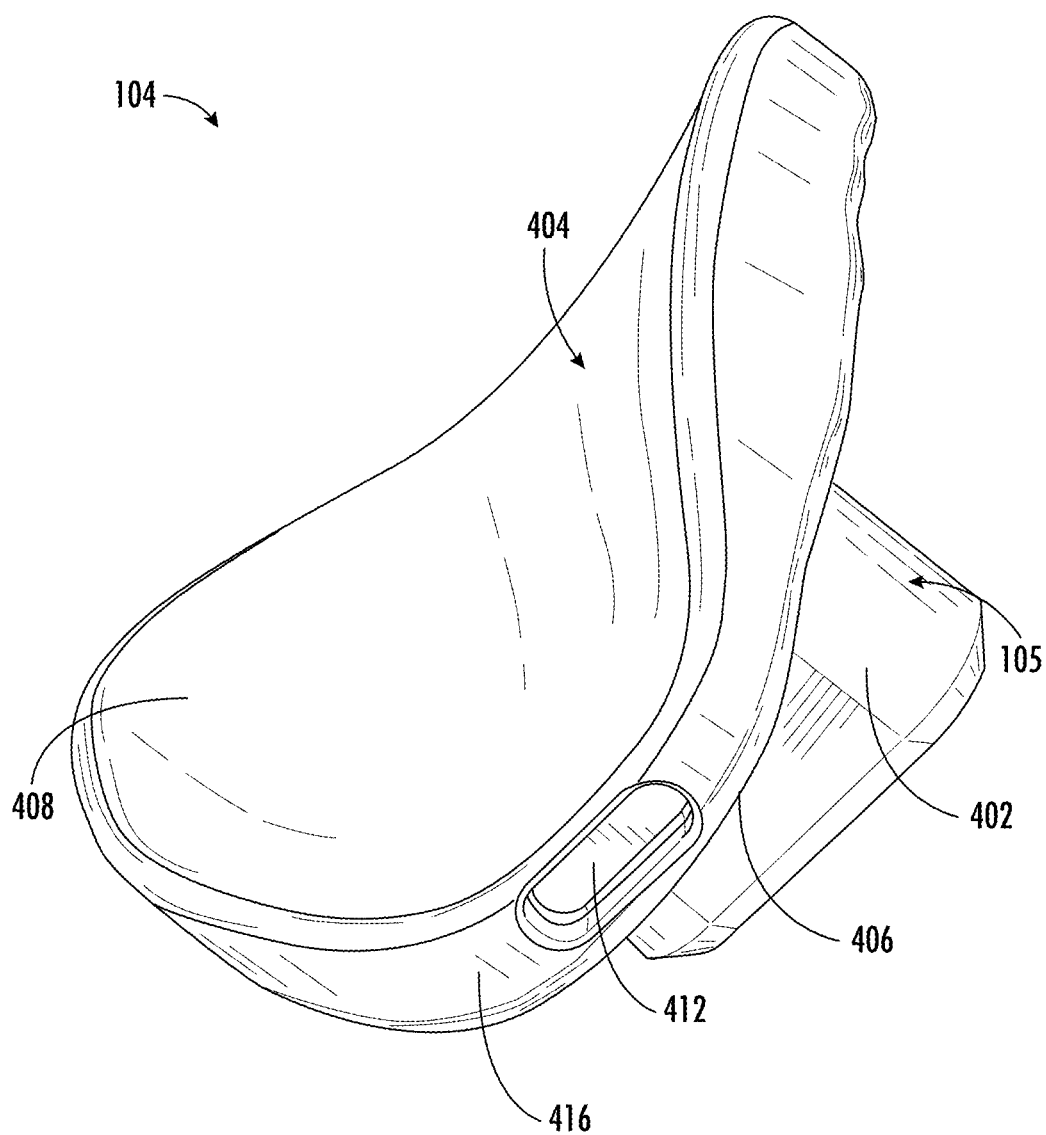
FIG. 13 is another perspective view of the trapezium implant of FIG. 9.

The implant head portion 404 can include one or more apertures as shown in, for example, FIGS. 10-11. The implant head portion 404 can include a first aperture 410 and a second aperture 412. The first aperture 410 can be disposed on a first lateral surface 414 of the implant head portion 404. The second aperture 412 can be disposed on a second lateral surface 416 of the implant head portion 404. The first lateral surface 414 and the second lateral surface 416 can be opposite each other. The first aperture 410 and the second aperture 412 can be configured to facilitate extraction and insertion of the trapezium implant 104.

Figure 15:
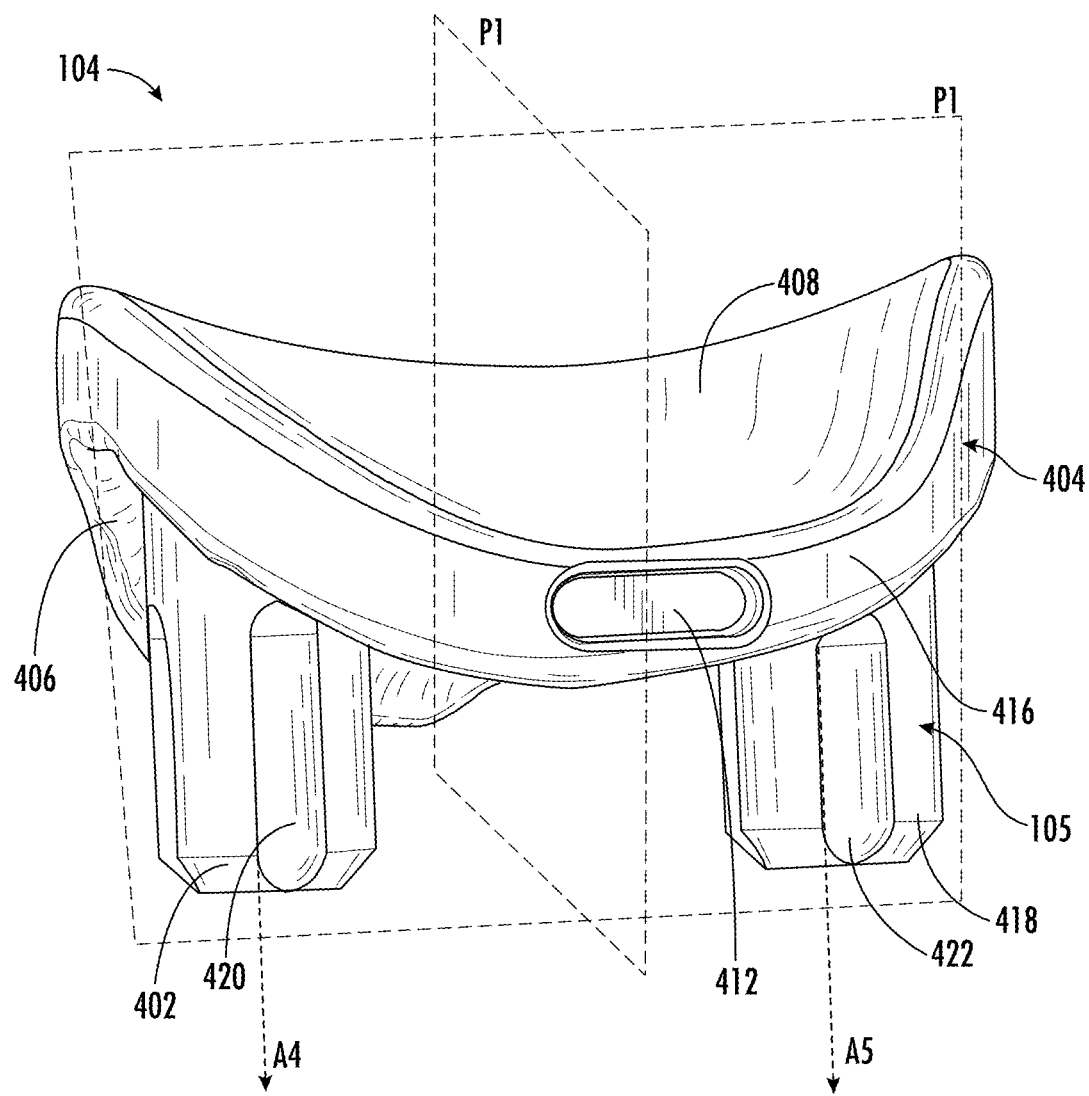
FIG. 15 is a perspective view of another trapezium implant.
Figure 16:
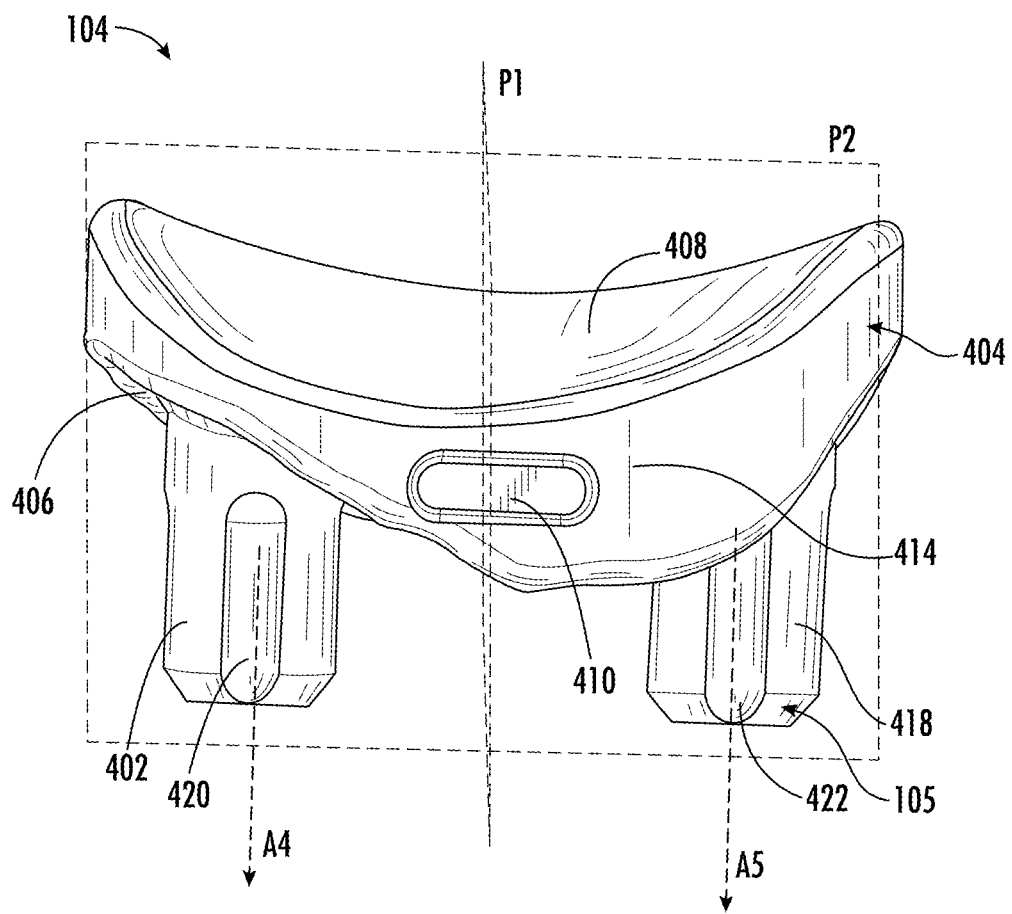
FIG. 16 is a front view of the trapezium implant of FIG. 15.
Figure 17:
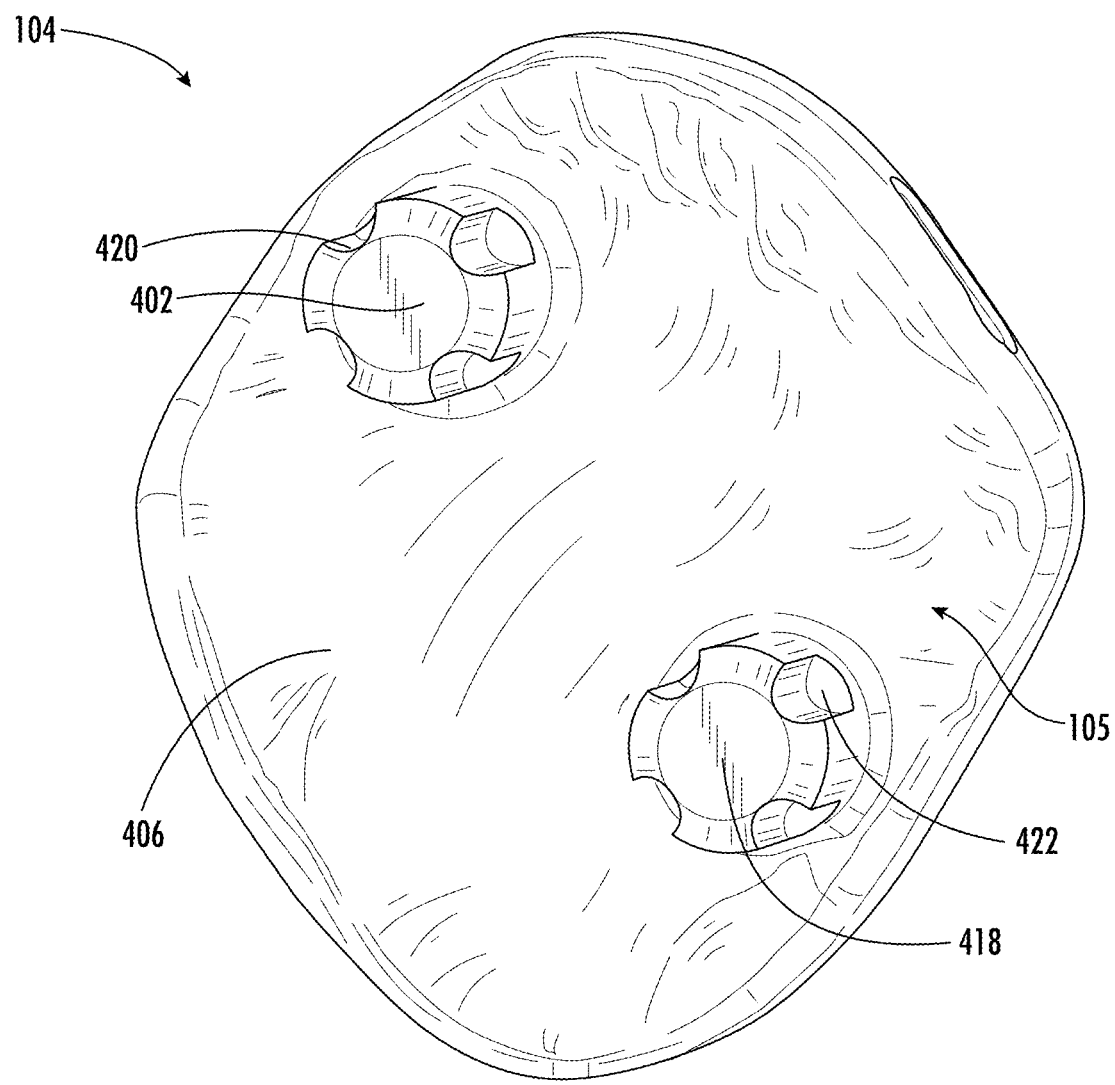
FIG. 17 is a bottom view of the trapezium implant of FIG. 15.

FIGS. 15-17 depicts an implementation of the trapezium implant 104 which can include one or more cavity inserts. The trapezium implant 104 can include the first cavity insert 402 and a second cavity insert 418 (e.g., pegs). The first cavity insert 402 and the second cavity insert 418 can enable durable, long-term fixation of the trapezium implant 104 to the trapezium bone 204 via bone ingrowth. The second cavity insert 418 can extend from the bottom surface 406. The second cavity insert 418 can have a cylindrical shape. In this case, the first cavity insert 402 can also have a cylindrical shape. The first cavity insert 402 can be centered on a fourth axis A4. The second cavity insert 418 can be centered on a fifth axis A5. The fourth axis A4 and the fifth axis A5 can be parallel to and offset from each other. The fourth axis A4 and the fifth axis A5 can be parallel to and offset from the first axis A1 and the second axis A2. In some implementations, the fourth axis A4 and the fifth axis A5 are co-axial and skewed from each other and, in some implementations, the first axis A1 and the second axis A2.

Figure 18:
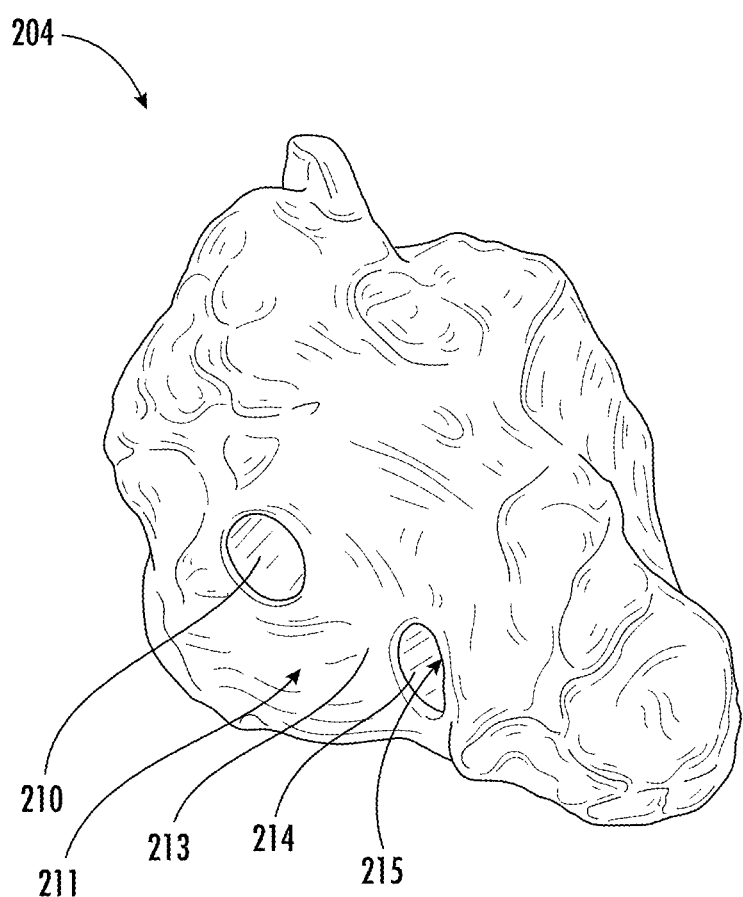
FIG. 18 is a perspective view of cavities of the trapezium bone.
Figure 19:
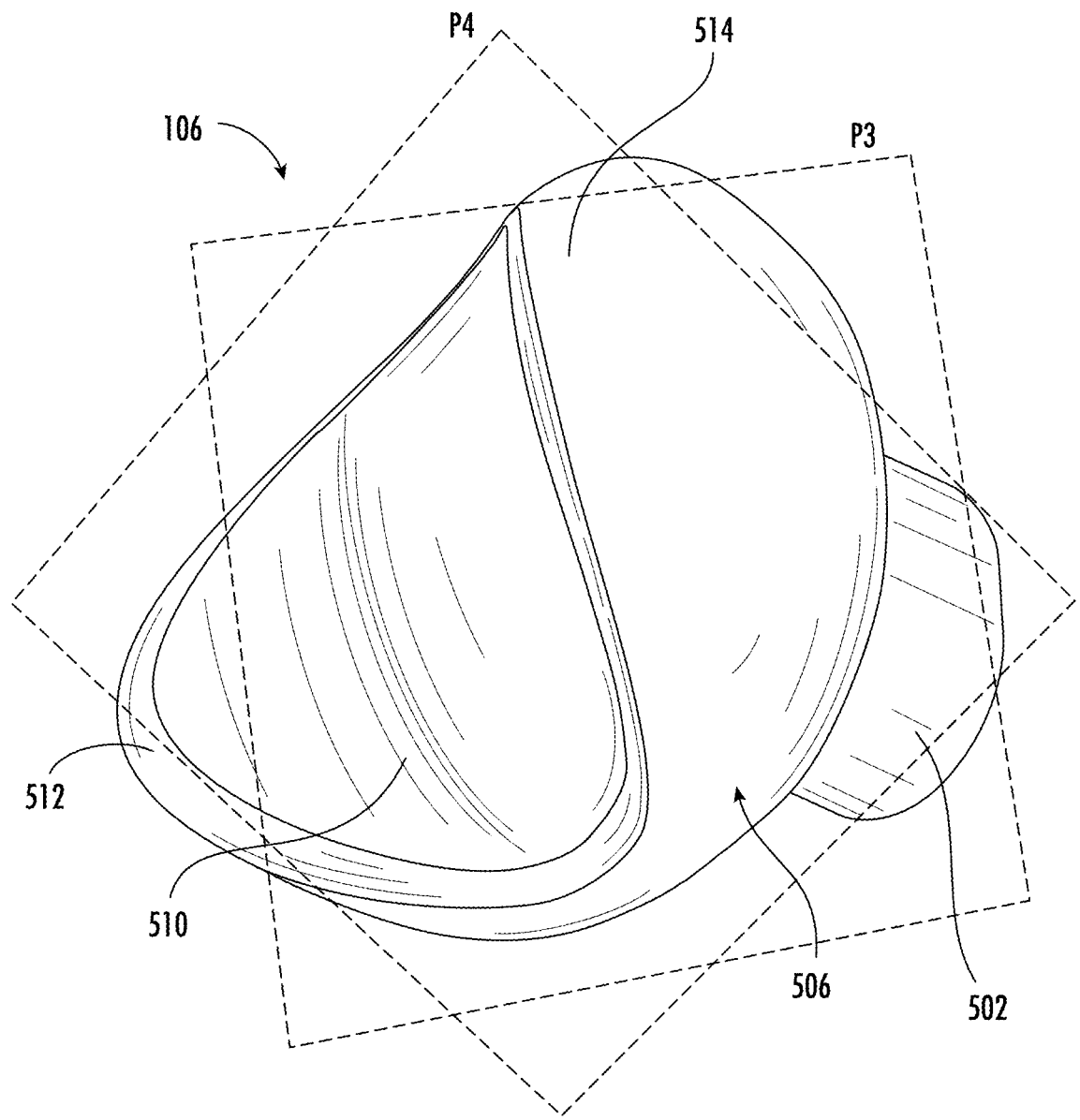
FIG. 19 is a perspective view of a spacer.
Figure 20:
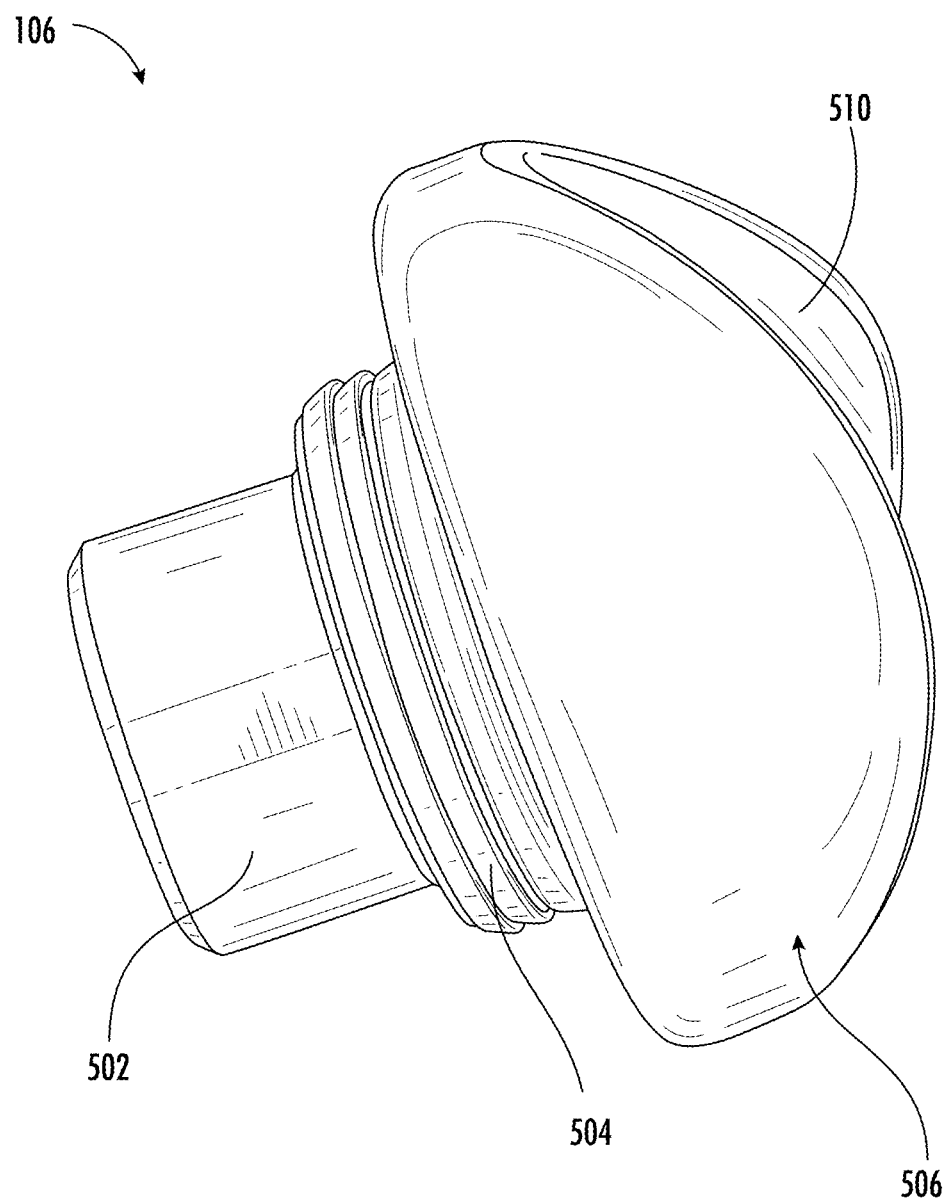
FIG. 20 is a side view of the spacer of FIG. 19.
Figure 21:
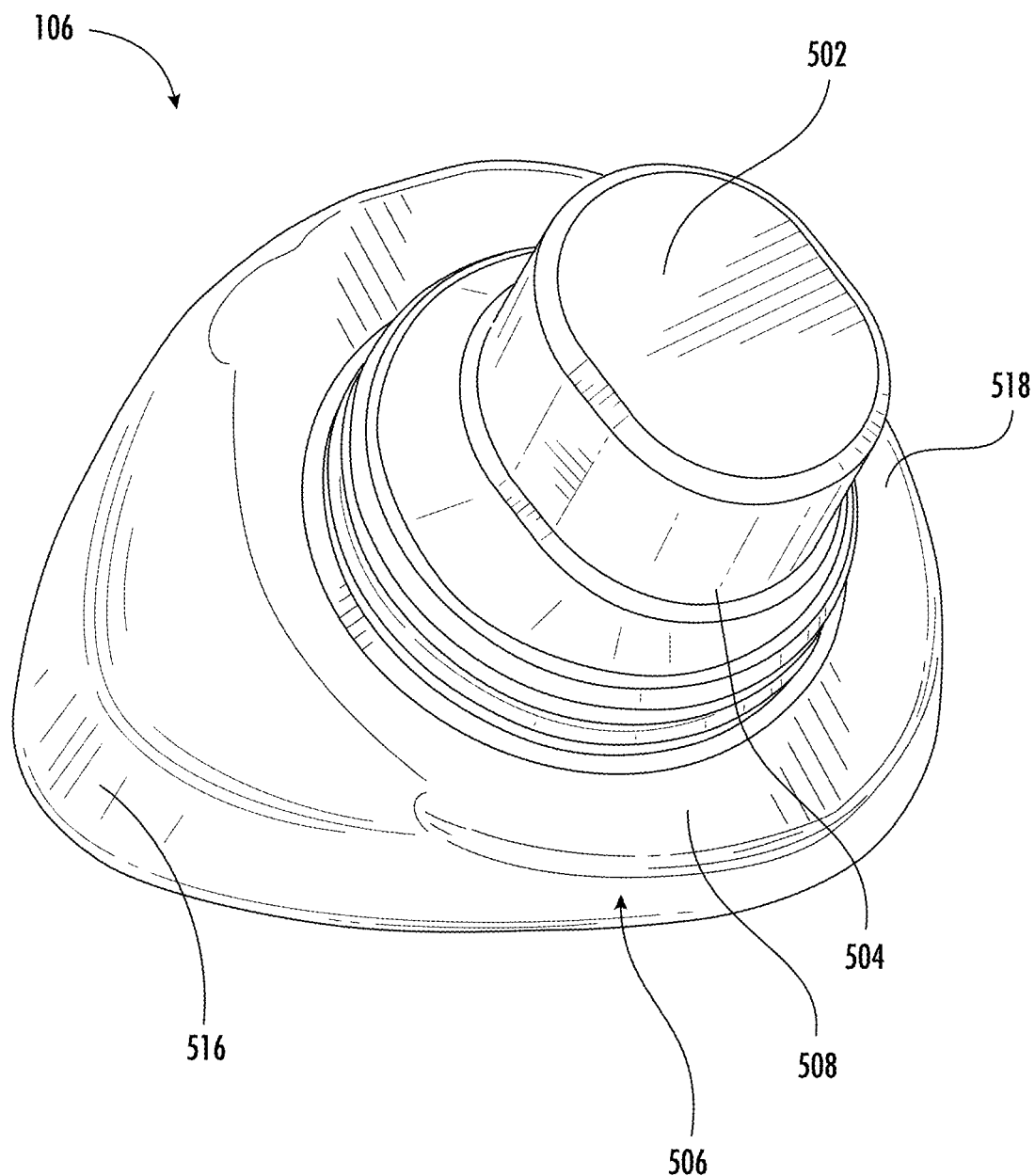
FIG. 21 is a perspective view of the spacer of FIG. 19.

In this case, the trapezium bone 204 can include a third cavity 214, shown in FIG. 18. The third cavity 214 can be centered on the fifth axis A5. The trapezium implant 104 can be inserted until the second cavity insert 418 contacts a bottom surface 215 of the third cavity 214. For example, the trapezium implant 104 is inserted until both the first cavity insert 402 and the second cavity insert 418 contacts the bottom surface 212 and the bottom surface 215, respectively. The second cavity 210, in this case, can be centered on the fourth axis A4. The third cavity 214 can be congruent to the second cavity insert 418. The second cavity 210 can be congruent to the first cavity insert 402. The first cavity insert 402 can include one or more first recesses 420 as shown in, for example, FIG. 15. The one or more first recesses 420 can be configured to facilitate the insertion and extraction of the trapezium implant 104 into the second cavity 210. The second cavity insert 418 can include one or more second recesses 422. The one or more second recesses 422 can be configured to facilitate the insertion and extraction of the trapezium implant 104 into the third cavity 214. For example, the one or more first recesses 420 and the one or more second recesses 422 can facilitate a press fit of the first cavity insert 402 and the second cavity insert 418 into the second cavity 210 and the third cavity 214, respectively.

In some implementations, the first cavity insert 402 and the second cavity insert 418 include CoCr on HCPE. The first cavity insert 402 and the second cavity insert 418 can enable reduced friction of the trapezium implant 104 to the trapezium bone 204 (e.g., compared to titanium).

The implant apparatus 100 can include a spacer 106. The spacer 106 is shown in greater detail in FIGS. 19-22. The spacer 106 can replicate the anatomy of the CMC joint. The spacer 106 can be coupled to and in contact with the metacarpal implant 102. The spacer 106 can be in contact with the trapezium implant 104. The spacer 106 can be snap fit to the metacarpal implant 102 via the second portion 318. In some implementations, the spacer 106 is press fit into the opening 314 to couple the spacer 106 and the metacarpal implant 102. The spacer 106 can include polyethylene (PE). The spacer 106 can include plastic, ceramic, metal, or any other material with a high wear and low friction characteristics, such as composites (e.g., carbon fiber-reinforced polymers). The spacer 106 can be configured to mimic an anatomy of the CMC joint and mitigate impingement of the metacarpal implant 102 and the trapezium implant 104. The spacer 106 can also mitigate impingement of the metacarpal bone 202 and the trapezium bone 204.

The spacer 106 can include an opening insert 502. The opening insert 502 can be inserted into the opening 314. The opening insert 502 can be in contact with the second portion 318 and, in some implementations, the third portion 320. The opening insert 502 can be congruent with the second portion 318. The opening insert 502 can be centered on the first axis A1. The opening insert 502 can be snap fit to the second portion 318. In some implementations, the opening insert 502 can be press fit to the second portion 318.

In some implementations, the opening insert 502 is threadedly coupled to the first portion 316. In this case, the spacer 106 includes a threaded portion 504 as shown in, for example, FIG. 20. The first portion 316, in this case, includes the first threaded portion 324. The opening insert 502 and the first portion 316 can be threadedly coupled via the threaded portion 504 and the first threaded portion 324. The threaded portion 504 has a circular shape. The threaded portion 504 can be centered on the second axis A2.

The spacer 106 can include a spacer head portion 506. The spacer head portion 506 can have a bottom surface 508. The opening insert 502 and, in some implementations, the threaded portion 504 can extend from the bottom surface 508. The bottom surface 508 can have a flat shape. The bottom surface 508 can be in contact with the radial lip 308. In some implementations, a length and a width of the bottom surface 508 is greater than a length and a width of the radial lip 308. The bottom surface 508 can have an elliptic shape as shown in, for example, FIG. 21.

The spacer head portion 506 can also have a top surface 510. The top surface 510 can have a smooth shape. The top surface 510 can be convex on a third plane P3 and concave on a fourth plane P4. The top surface 510 can be congruent to the top surface 408 of the implant head portion 404. The top surface 510 can be aligned with the top surface 408 as shown in, for example. FIG. 1. The third plane P3 can be at an angle respective to the second plane P2. The fourth plane P4 can be at an angle respective to the first plane P1. The top surface 510 can be centered on and in contact with the implant head portion 404, while the bottom surface 508 and the opening insert 502 are centered on and in contact with the opening 314. For example, the trapezium implant 104 includes the first cavity insert 402 centered on the third axis A3, and the metacarpal implant 102 includes the second portion 318 centered on the first axis A1, and the first portion 316 centered on the second axis A2. In this case, the opening insert 502 is centered on the first axis A1, and the top surface 510 is centered on the third axis A3. In some implementations, the threaded portion 504 is centered on the second axis A2.

Figure 22:
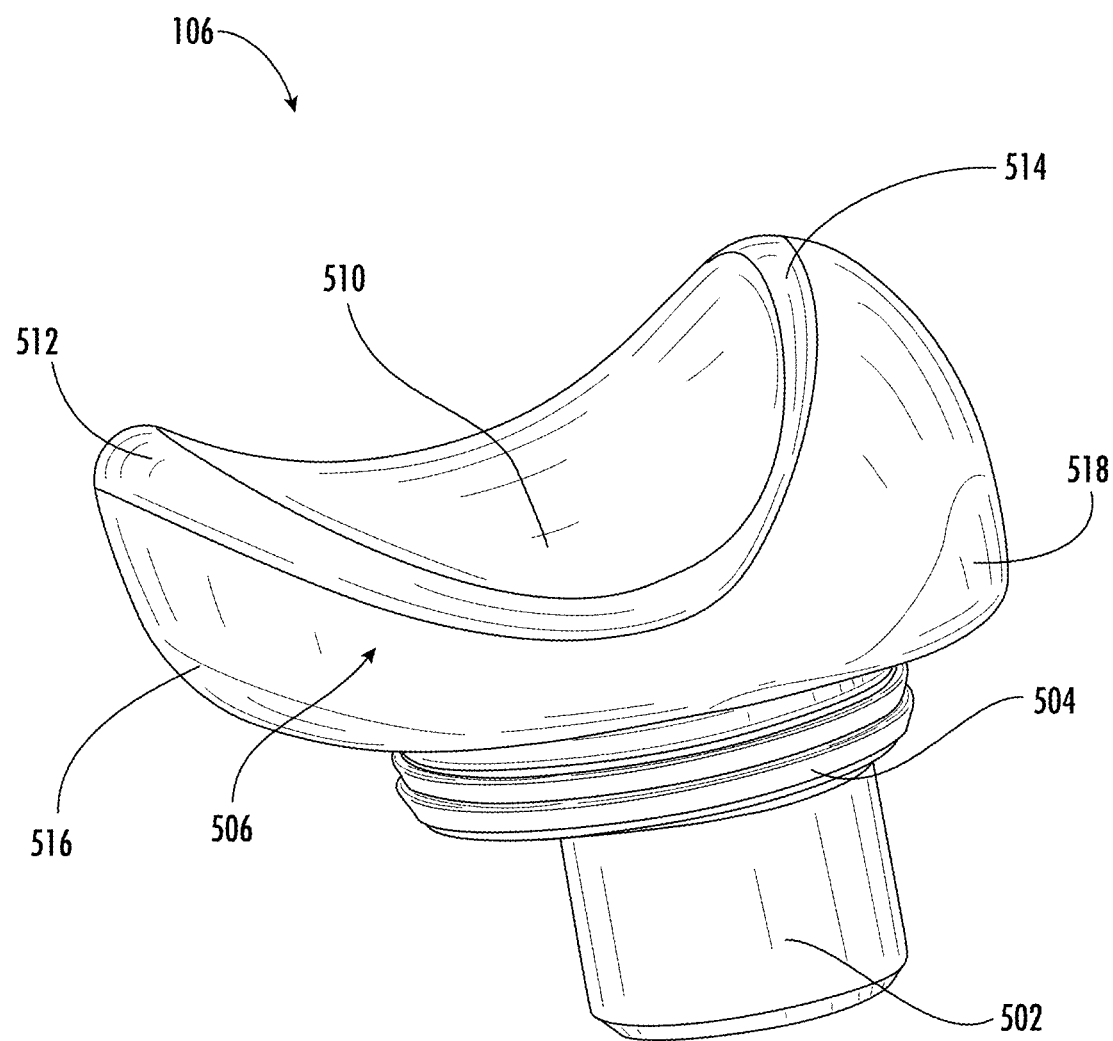
FIG. 22 is another side view of the spacer of FIG. 19.

The top surface 510 can include one or more apexes as shown in, for example, FIG. 22. The top surface 510 can include a first apex 512 and a second apex 514. The first apex 512 can be located along the fourth plane P4. The second apex 514 can be located along the fourth plane P4. The second apex 514 can have a height greater than a height of the first apex 512.

The spacer head portion 506 can include a first end 516. The spacer head portion 506 can include a second end 518. The first end 516 can extend further away from the opening insert 502 than the second end 518 as shown in, for example, FIG. 22. In some implementations, the second end 518 extends further away from the third axis A3 than the first end 516. The second end 518 can extend further away from the top surface 510 than the first end 516. The first apex 512 can be located closer to the first end 516 than the second end 518. The second apex 514 can be located closer to the second end 518 than the first end 516.

Figure 23:
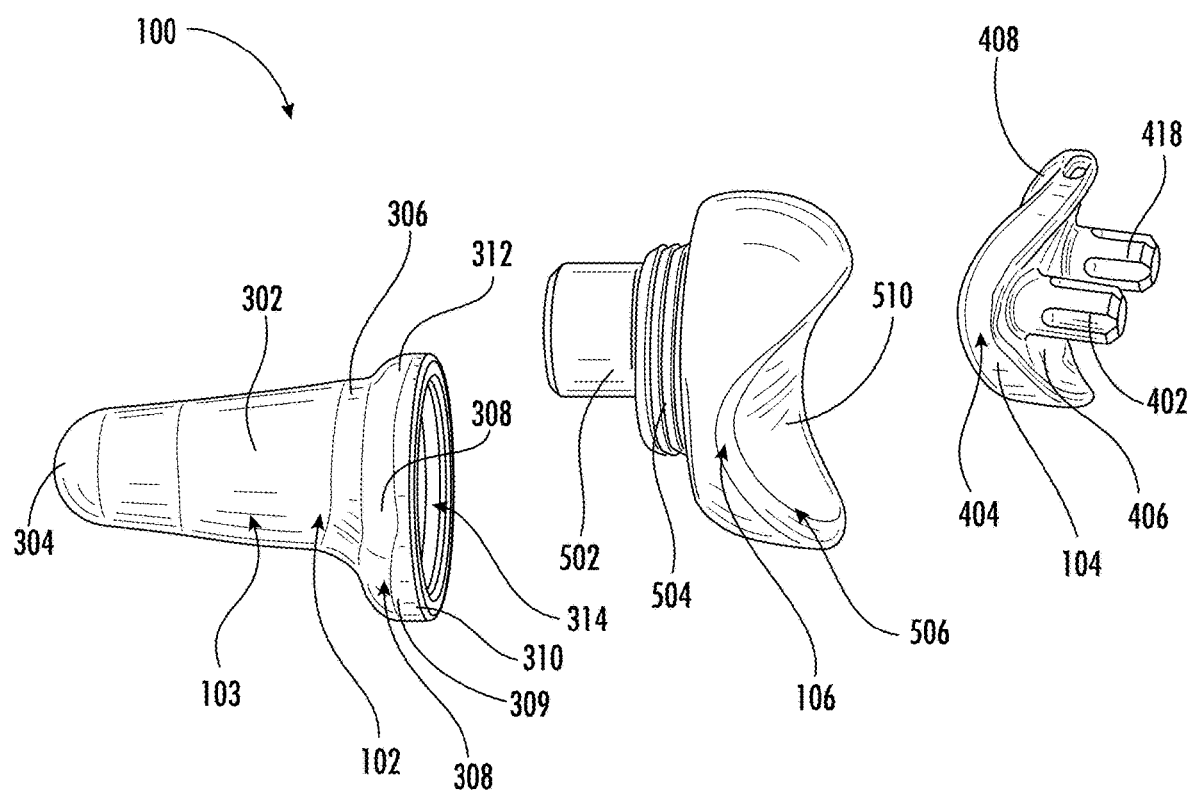
FIG. 23 is an exploded view of an implant system.

As shown in, for example, FIG. 23, the spacer 106 is located between the metacarpal implant 102 and the trapezium implant 104. The opening insert 502 and the threaded portion 504 are inserted into the opening 314 of the metacarpal implant 102. The top surface 510 of the spacer 106 is in contact with the top surface 408. The top surface 510 can be congruent to the top surface 408. As shown in, for example, FIG. 2, the metacarpal implant 102 can be covered by the metacarpal bone 202. At least the top surface 510 and the top surface 408 may not be in contact with either the metacarpal bone 202 or the trapezium bone 204. A fixation of the metacarpal implant 102 to the metacarpal bone 202 can enable bone ingrowth into the implant apparatus 100. A fixation of the trapezium implant 104 to the trapezium bone 204 can also enable bone ingrowth into the implant apparatus 100.

Figure 24:
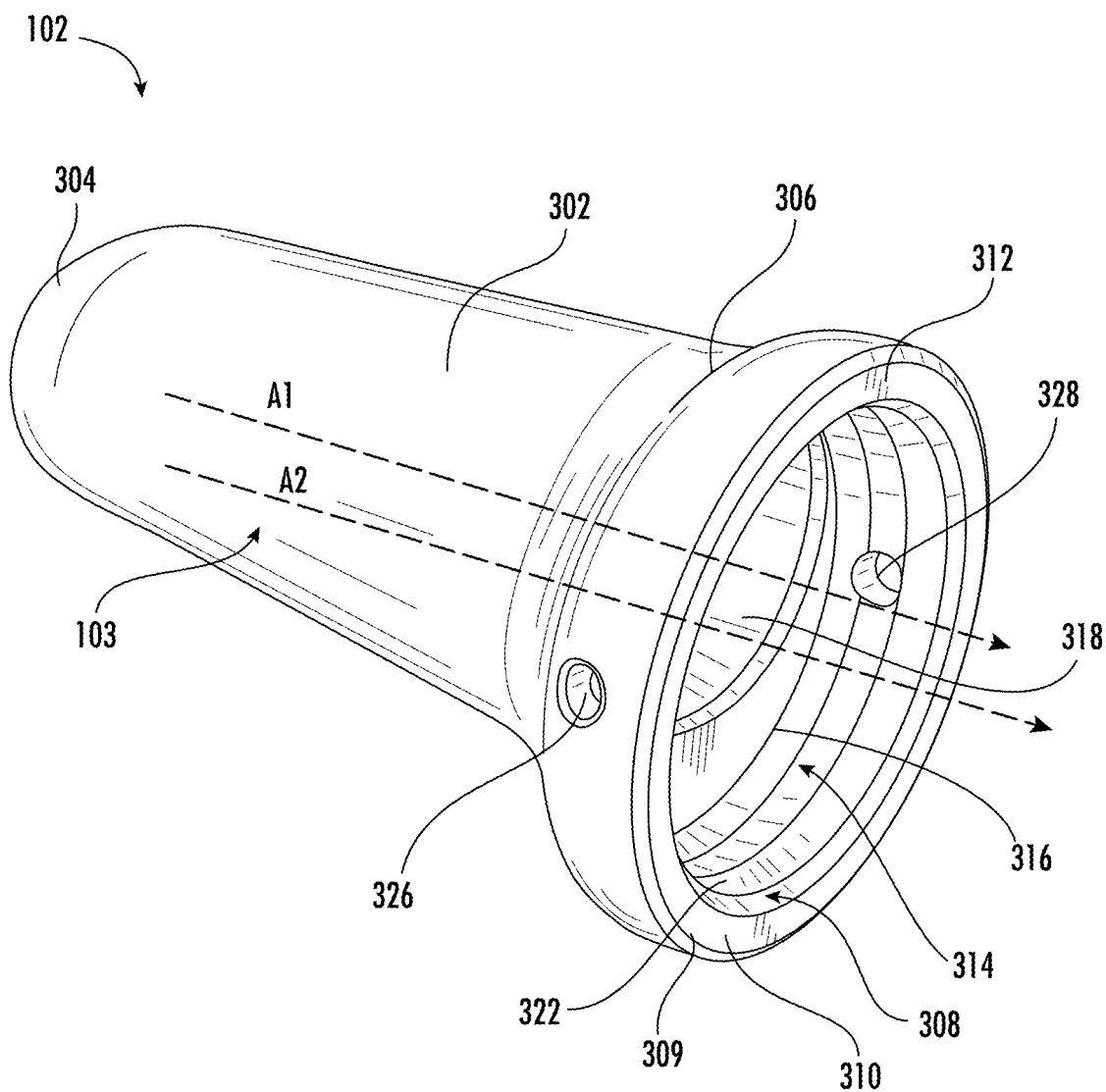
FIG. 24 is a perspective view of an example metacarpal implant.

Referring now to FIG. 24, the metacarpal implant 102 can include one or more apertures. The metacarpal implant 102 can include a first aperture 326 and a second aperture 328. A suture may be threaded through and/or around at least one of the first aperture 326 and the second aperture 328 to reattach an abductor pollicis longus (APL) tendon. For example, during an implantation procedure of implant apparatus 100, the APL tendon may be moved (e.g., taken down) for exposure (e.g., to the metacarpal bone 202). Furthermore, in a revision setting (e.g., making adjustments to the implant apparatus 100), the trapezium bone 204 can be excised and a procedure can be converted from the implantation procedure to a trapeziectomy and/or suspension arthroplasty without removing the metacarpal implant 102 by drilling through the first aperture 326 and the second aperture 328. The first aperture 326 and the second aperture 328 may be located on the radial lip 308. The first aperture 326 and the second aperture 328 may be located on opposite sides of the radial lip 308. The first aperture 326 and the second aperture 328 may be equidistant from the second axis A2. The first aperture 326 may have a radius equal to the second aperture 328.

The first aperture 326 and the second aperture 328 may have a round, oblong, square, or any other shape that facilitates attachment of sutures or screws. In some implementations, the metacarpal implant 102 includes at least three apertures at a distance apart that allows sutures to past in and out of the metacarpal implant 102 on a same side. For example, the first aperture 326 can be two apertures and the second aperture 328 can be two apertures located on opposite sides of the metacarpal implant 102.

The first aperture 326 and the second aperture 328 enable repair of the APL to a base of the metacarpal bone 202 in cases that the APL is released for exposure (e.g., wrist arthroscopy). Furthermore, in cases of infection, loosening, or other modes of failure and no new implant (e.g., the implant apparatus 100) can be inserted, the first aperture 326 and the second aperture 328 can be used to create a suspension arthroplasty for the thumb and reconstruct an intermetacarpal ligament of the thumb.

Figure 25:
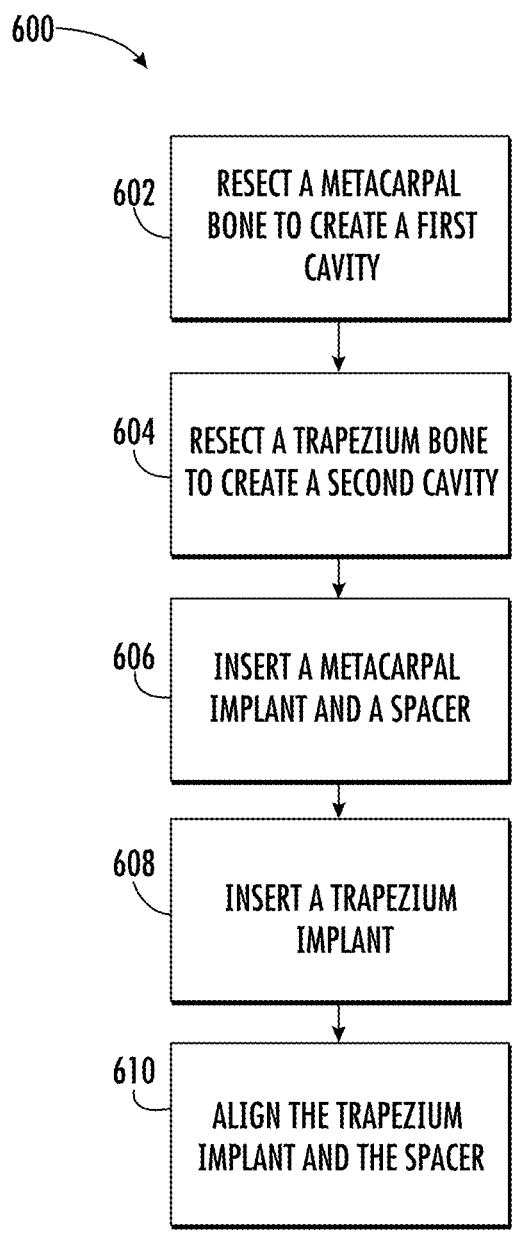
FIG. 25 is a flow diagram of a method for performing a joint replacement.

FIG. 25 is a block diagram of a method 600 for implanting a prosthesis (e.g., the implant apparatus 100). The method 600 can be performed with a kit including a rasp, a contouring tool, and the prosthesis. The method 600 or portions thereof can be performed by any of various actors, such as one or more surgeons, physicians, medical professionals, automated or robotic surgical devices, tools, or systems, or various combinations thereof. The method 600 can be performed at least as part of a joint replacement procedure. The prosthesis can include a metacarpal implant (e.g., the metacarpal implant 102), a trapezium implant (e.g., the trapezium implant 104), and a spacer (e.g., the spacer 106).

At block 602, the method 600 can include resecting a portion (e.g., the portion 203) of a metacarpal bone (e.g., the metacarpal bone 202) to create a first cavity (e.g., the first cavity 206). Resection of the portion of the metacarpal bone can be performed using the rasp. Resecting the portion can start at a surface (e.g., the surface 205) of the metacarpal bone facing a trapezium bone (e.g., the trapezium bone 204).

At block 604, the method 600 can include resecting a portion (e.g., the portion 211) of the trapezium bone to create a second cavity (e.g., the second cavity 210). Resection of the portion of the trapezium bone can be performed using the rasp. Resecting the portion can start at a surface (e.g., the surface 213) of the trapezium bone facing the metacarpal bone.

At block 606, the method 600 can include inserting, the metacarpal implant and the spacer. The spacer can be coupled to the metacarpal implant. The metacarpal implant can then be inserted into the first cavity until a stem (e.g., the stem 302) contacts an inner surface of the first cavity (e.g., the bottom surface 208). The inner surface of the first cavity can also be contoured to form a mating engagement (e.g., couple) the metacarpal implant with the metacarpal bone. The contouring can be performed using the contouring tool.

At block 608, the method 600 can include inserting, the trapezium implant into the second cavity. The trapezium implant can be inserted until a first cavity insert (e.g., the first cavity insert 402) of the trapezium implant contacts an inner surface of the second cavity (e.g., the bottom surface 212). The inner surface of the second cavity can also be contoured to form a mating engagement (e.g., couple) the trapezium implant with the trapezium bone. The contouring can be performed using the contouring tool.

At block 610, the method 600 can include aligning a top surface (e.g., the top surface 408) of the trapezium implant and a top surface (e.g., the top surface 510) of the spacer. Aligning the top surfaces of the trapezium implant and the top surface can ensure anatomy preservation of the CMC joint. In some implementations, the method 600 can also include resecting a third cavity (e.g., the third cavity 214) in the trapezium bone. In this case, the trapezium implant includes a second cavity insert (e.g., the second cavity insert 418). The trapezium implant can thus be inserted into both the second cavity and the third cavity. The trapezium implant is inserted until both the first cavity insert and the second cavity insert contact the inner surface of the second cavity and an inner surface of the third cavity (e.g., the bottom surface 215), respectively.

While this specification contains many specific implementation details, these should not be construed as limitations on the scope of what can be claimed but rather as descriptions of features specific to particular implementations. Certain features described in this specification in the context of separate implementations can also be implemented in combination in a single implementation. Conversely, various features described in the context of a single implementation can also be implemented in multiple implementations separately or in any suitable subcombination. Moreover, although features can be described as acting in certain combinations and even initially claimed as such, one or more features from a claimed combination can, in some cases, be excised from the combination, and the claimed combination can be directed to a subcombination or variation of a subcombination.

As utilized herein, the terms "substantially," "generally," "approximately," "about," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the appended claims.

The term "coupled" and the like, as used herein, mean the joining of two components directly or indirectly to one another. Such joining can be stationary (e.g., permanent) or moveable (e.g., removable or releasable). Such joining can be achieved with the two components or the two components and any additional intermediate components being integrally formed as a single unitary body with one another, with the two components, or with the two components and any additional intermediate components being attached to one another.

It is important to note that the construction and arrangement of the various systems shown in the various example implementations is illustrative only and not restrictive in character. All changes and modifications that come within the spirit and/or scope of the described implementations are desired to be protected. It should be understood that some features may not be necessary, and implementations lacking the various features can be contemplated as within the scope of the disclosure, the scope being defined by the claims that follow. When the language "a portion" is used, the item can include a portion and/or the entire item unless specifically stated to the contrary.

Also, the term "or" is used, in the context of a list of elements, in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. can be either X, Y, Z, X and Y, X and Z, Y and Z, or X, Y, and Z (i.e., any combination of X, Y, and Z). Thus, such conjunctive language is not generally intended to imply that certain implementations require at least one of X, at least one of Y, and at least one of Z to each be present, unless otherwise indicated.

Additionally, the use of ranges of values (e.g., W1 to W2, etc.) herein are inclusive of their maximum values and minimum values (e.g., W1 to W2 includes W1 and includes W2, etc.), unless otherwise indicated. Furthermore, a range of values (e.g., W1 to W2, etc.) does not necessarily require the inclusion of intermediate values within the range of values (e.g., W1 to W2 can include only W1 and W2, etc.), unless otherwise indicated.

What is claimed is:

1. An apparatus, comprising:
a metacarpal implant comprising:
a stem configured to be inserted into a first cavity of a metacarpal bone and having a first end and a second end, the stem centered on an axis;
a radial lip extending from the second end;
an opening extending from the radial lip to the first end, wherein the stem comprises an inner stem wall facing the opening and the radial lip comprises an outer wall and an inner lip wall facing the opening, the inner lip wall further from the axis than the inner stem wall;
a first aperture extending through the radial lip from the outer wall to the inner lip wall; and
a second aperture extending through the radial lip from the outer wall to the inner lip wall;
a trapezium implant comprising:
an implant head portion, the implant head portion having a top surface and a bottom surface, the top surface and the bottom surface being convex on a first plane and concave on a second plane, the top surface having a smooth shape and the bottom surface having a shape to match a shape of a trapezium bone; and
a first cavity insert, configured to be inserted into a second cavity of the trapezium bone extending from the bottom surface; and
a spacer comprising:
a spacer head portion congruent to the implant head portion, the spacer head portion having a top surface and a bottom surface, the top surface having a smooth shape and being convex on a third plane and concave on a fourth plane; and
an opening insert to be inserted in the opening and extending from the bottom surface.

2. The apparatus of claim 1, wherein the metacarpal implant and the trapezium implant comprise at least one of titanium, ceramic, or pyrolytic carbon.

3. The apparatus of claim 1, wherein the spacer comprises at least one of a plastic, ceramic, metal, or pyrolytic carbon.

4. The apparatus of claim 1, wherein the bottom surface of the implant head portion comprises cobalt chrome (CoCr) on highly crosslinked polyethylene (HCPE).

5. The apparatus of claim 1, wherein the trapezium implant includes a second cavity insert, the second cavity insert extending from the bottom surface, the first cavity insert extending along a first axis and the second cavity insert extending along a second axis, the first axis and the second axis offset from each other and parallel.

6. The apparatus of claim 1, wherein the top surface of the spacer head portion and the top surface of the implant head portion are congruent.

7. The apparatus of claim 1, wherein the implant head portion further comprises a first aperture and a second aperture, the first and the second aperture disposed on a first lateral surface and a second lateral surface of the implant head portion, the first lateral surface and the second lateral surface being opposite each other.

8. The apparatus of claim 1, wherein the stem and the first cavity are congruent.

9. The apparatus of claim 1, wherein a first end of the spacer head portion extends further away from the opening insert than a second end of the spacer head portion.

10. The apparatus of claim 1, wherein a first portion of the radial lip extends further away from the stem than a second portion on the radial lip.

11. The apparatus of claim 1, wherein the opening comprises a first portion, a second portion, and a third portion, the first portion located within the radial lip and the second portion and the third portion located within the stem.

12. An apparatus, comprising:
a metacarpal implant comprising:
a stem configured to be inserted into a first cavity of a metacarpal bone and having a first end and a second end;
a radial lip extending from the second end;
an opening extending from the radial lip to the first end, wherein the stem comprises an inner stem surface facing the opening and the radial lip comprises an outer surface and an inner lip surface facing the opening, the inner stem surface and the inner lip surface connected by a surface perpendicular to the inner stem surface;
a first aperture extending through the radial lip from the outer surface to the inner lip surface; and
a second aperture extending through the radial lip from the outer surface to the inner lip surface; and
a spacer comprising:
a spacer head portion having a top surface and a bottom surface, the top surface having a smooth shape and being convex on a third plane and concave on a fourth plane; and
an opening insert to be inserted in the opening and extending from the bottom surface.

13. The apparatus of claim 12, wherein the radial lip extends radially outwards from the stem.

14. A metacarpal implant comprising:
a stem configured to be inserted into a first cavity of a metacarpal bone and having a first end and a second end, the second end comprising a seat;
a radial lip extending radially outwards from the seat;
an opening extending from the radial lip to the first end and comprising a first portion, a second portion, and a third portion, the first portion located within the radial lip and the second portion and the third portion located within the stem, the seat extending from the second portion and connecting the first portion and the second portion;
a first aperture extending through the radial lip; and
a second aperture extending through the radial lip.

15. The metacarpal implant of claim 14, wherein:
the stem is centered on a first axis;
the radial lip is centered on a second axis parallel and offset from the first axis; and
the second aperture is located closer to the first axis than the second axis.

16. The metacarpal implant of claim 15, wherein the first aperture and the second aperture are equidistant from the first axis.

17. The metacarpal implant of claim 15, wherein the first portion is centered on the second axis and the second portion and the third portion are centered on the first axis.

18. The metacarpal implant of claim 14, wherein a dimension of the first portion is greater than a dimension of the second portion, and the dimension of the second portion is greater than a dimension of the third portion.

19. The metacarpal implant of claim 14, wherein a surface of the seat is perpendicular to an inner surface of the second portion.

\* \* \* \* \*